(12) United States Patent
Clark et al.

(10) Patent No.: US 6,355,813 B1
(45) Date of Patent: Mar. 12, 2002

(54) PROCESS OF MAKING 3-PHENYL-1-METHYLENEDIOXYPHENYL-INDANE-2-CARBOXYLIC ACID DERIVATIVES

(75) Inventors: William Morrow Clark, Philadelphia; Ivan Lantos, Wayne; Robert John Mills, Norristown; Lendon Norwood Pridgen, Collegeville; Ann Marie Tickner, Norristown, all of PA (US)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 09/607,173

(22) Filed: Jun. 29, 2000

Related U.S. Application Data

(62) Division of application No. 08/776,804, filed as application No. PCT/US96/18465 on Nov. 8, 1996, now Pat. No. 6,143,907.
(60) Provisional application No. 60/006,331, filed on Nov. 8, 1995.

(51) Int. Cl.$^7$ .................. C07D 317/70; C07C 41/00
(52) U.S. Cl. .................. 549/432; 568/630; 568/648; 568/649; 568/656
(58) Field of Search .................. 549/432; 568/630, 568/648, 649, 656

(56) References Cited

U.S. PATENT DOCUMENTS

| 5,389,620 A | 2/1995 | Ishikawa et al. ............... 514/80 |
| 6,114,549 A | * 9/2000 | Wood et al. ............... 549/432 |

FOREIGN PATENT DOCUMENTS

| WO | WO 93/08799 | 5/1993 |

* cited by examiner

*Primary Examiner*—Amelia Owens
(74) *Attorney, Agent, or Firm*—Kathryn L. Sieburth; Mary E. McCarthy; Charles M. Kinzig

(57) ABSTRACT

Invented is an improved process for preparing aromatic ring-fused cyclopentane derivatives. Preferred compounds prepared by this invention are indane carboxylates and cyclopentanopyridine derivatives. The most preferred compounds prepared by this invention are (+)(1S, 2R, 3S)-3-[2-(2-hydroxyeth-1-yloxy)-4-methoxyphenyl]-1-(3,4-methylenedioxyphenyl)-5-(prop-1-yloxy)indane-2-carboxylic acid and pharmaceutically acceptable salts thereof and (+)(1S, 2R, 3S)-3-(2-carboxymethoxy-4-methoxyphenyl)-1-(3,4-methylenedioxyphenyl)-5-(prop-1-yloxy)indane-2-carboxylic acid and pharmaceutically acceptable salts thereof. Also invented are novel intermediates useful in preparing these compounds.

4 Claims, No Drawings

PROCESS OF MAKING 3-PHENYL-1-METHYLENEDIOXYPHENYL-INDANE-2-CARBOXYLIC ACID DERIVATIVES

This application is a DIV of 08/776,804 filed Feb. 4, 1997 now U.S. Pat. No. 6,143,907, which is a 371 of PCT/US96/18465 filed Nov. 8, 1996 and claims the benefit of provisional application No. 60/006,331 filed Nov. 8, 1995.

The present invention relates to an improved process for preparing aromatic ring-fused cyclopentane derivatives. Preferably, the present invention relates to an improved process for preparing indane carboxylates and cyclopentanopyridine derivatives. Advantageously, the present invention relates to an improved process for preparing (+) (1S, 2R, 3S)-3-[2-(2-hydroxyeth-1-yloxy)-4-methoxyphenyl]-1-(3,4-methylenedioxyphenyl)-5-(prop-1-yloxy)indane-2-carboxylic acid and pharmaceutically acceptable salts thereof and (+) (1S, 2R, 3S)-3-(2-carboxymethoxy-4-methoxyphenyl)-1-(3,4-methylenedioxyphenyl)-5-(prop-1-yloxy)indane-2-carboxylic acid and pharmaceutically acceptable salts thereof. Such compounds are described in International Application Number: PCT/US94/04603-International Publication Number WO 94/25013 published on Nov. 10, 1994 and in U.S. Pat. No. 5,389,620, as being useful as endothelin receptor antagonists. Also invented are novel intermediates useful in preparing these compounds.

BACKGROUND OF THE INVENTION

Processes for the preparation of indane carboxylates, specifically (+) (1S, 2R, 3S)-3-[2-(2-hydroxyeth-1-yloxy)-4-methoxyphenyl]-1-(3,4-methylenedioxyphenyl)-5-(prop-1-yloxy)indane-2-carboxylic acid and (+) (1S, 2R, 3S)-3-(2-carboxymethoxy-4-methoxyphenyl)-1-(3,4-methylenedioxyphenyl)-5-(prop-1-yloxy)indane-2-carboxylic acid have previously been described. In particular a multistep process to prepare (+) (1S, 2R, 3S)-3-(2carboxymethoxy-4-methoxyphenyl)-1-(3,4-methylenedioxyphenyl)-5-(prop-1-yloxy)indane-2-carboxylic acid in 6% overall yield (not including a racemic separation step) from methyl 3-(prop-1-yloxy) benzoylacetate and a multistep process to prepare (+) (1S, 2R, 3S)-3-[2-(2-hydroxyeth-1-yloxy)-4-methoxyphenyl]-1-(3,4 -methylenedioxyphenyl)-5-(prop-1-yloxy)indane-2-carboxylic acid in 2% overall yield (not including a racemic separation step) from methyl 3-(prop-1 -yloxy) benzoylacetate is reported in International Publication Number WO 4/25013, published Nov. 10, 1994. The syntheses of these molecules are complicated by the presence of three chiral centers in each compound.

Processes for the preparation of cyclopentanopyridine derivatives have previously been described. In particular, multistep processes to prepare cyclopentanopyridine derivatives, in low over all yield, are reported in U.S. Pat. No. 5,389,620.

Thus, there is a need in the art for an economical method to prepare indane carboxylates and cyclopentanopyridine derivatives, specifically (+) (1S, 2R, 3S)-3-[2-(2-hydroxyeth-1-yloxy)-4-methoxyphenyl]-1-(3,4-methylenedioxyphenyl)-5-(prop-1-yloxy)indane-2-carboxylic acid and pharmaceutically acceptable salts thereof and (+) (1S, 2R, 3S)-3-(2-carboxymethoxy-4-methoxyphenyl)-1-(3,4-methylenedioxyphenyl)-5-(prop-1-yloxy)indane-2-carboxylic acid and pharmaceutically acceptable salts thereof.

The numerous advantages of the presently invented process and intermediates will become apparent upon review of the following description.

SUMMARY OF THE INVENTION

This invention relates to an improved process for preparing aromatic ring-fused cyclopentane derivatives.

This invention also relates to novel intermediates useful in preparing aromatic ring-fused cyclopentane derivatives.

This invention relates to an improved process for preparing indane carboxylates.

This invention also relates to novel intermediates useful in preparing indane carboxylates.

This invention relates to an improved process for preparing cyclopentanopyridine derivatives.

This invention also relates to novel intermediates useful in preparing cyclopentanopyridine derivatives.

This invention relates to an improved process for preparing (+) (1S, 2R, 3S)-3-(2-(2-hydroxyeth-1-yloxy)-4-methoxyphenyl]-1-(3,4-methylenedioxyphenyl)-5-(prop-1-yloxy)indane-2-carboxylic acid and pharmaceutically acceptable salts thereof, preferably the ethylene diamine 2:1 salt.

This invention relates to novel intermediates useful in preparing (+) (1S, 2R, 3S)-3-[2-(2-hydroxyeth-1-yloxy)-4-methoxyphenyl]-1-(3,4-methylenedioxyphenyl) -5-(prop-1-yloxy)indane-2-carboxylic acid.

This invention relates to an improved process for preparing (+) (1S, 2R, 3S)-3-(2-carboxymethoxy-4-methoxyphenyl)-1-(3,4-methylenedioxyphenyl)-5-(prop-1-yloxy)indane-2-carboxylic acid and pharmaceutically acceptable salts thereof, preferably the disodium salt.

This invention relates to novel intermediates useful in preparing (+) (1S, 2R, 3S)-3-(2-carboxymethoxy-4-methoxyphenyl)-1-(3,4-methylenedioxyphenyl)-5-(prop-1-yloxy)indane-2-carboxylic acid.

DETAILED DESCRIPTION OF THE INVENTION

Unless otherwise defined, the term 'aromatic ring-fused cyclopentane derivatives' as used herein, is meant the racemic compounds of Formula (1):

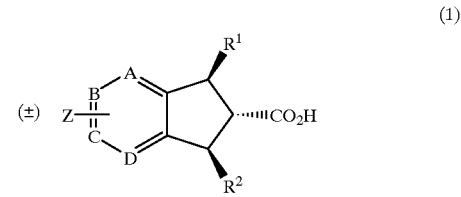

wherein A, B, C and D are carbon atoms or three of A, B, C and D are carbon atoms and one is a nitrogen atom;

$R^1$ is

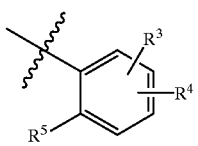

where $R^3$ and $R^4$ are independently H, OH, protected OH, $C_{1-8}$alkoxy, I, Br, Cl, F, $CF_3$ or $C_{1-6}$alkyl and $R^5$ is —$OCH_2CO_2H$ or —$OCH_2CH_2OH$;

$R^2$ is

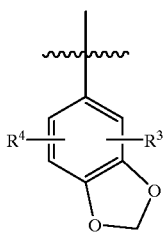

where $R^3$ and $R^4$ are as indicated above and

Z is H, OH, or $C_{1-5}$alkoxy;

or a pharmaceutically acceptable salt thereof.

Preferred among the racemic compounds of Formula (1) are the compounds of Formula (17):

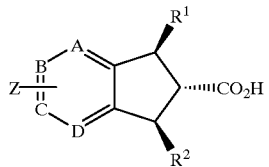

(17)

wherein A, B, C, D, $R^1$, $R^2$ and Z are as described in Formula (1);

or a pharmaceutically acceptable salt thereof.

By the term indane carboxylates as used herein is meant the racemic compounds of: Formula (2):

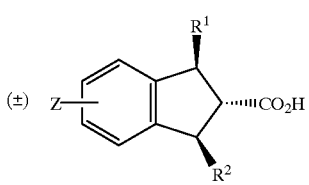

(2)

wherein $R^1$, $R^2$ and Z are as described in Formula (1);

or a pharmaceutically acceptable salt thereof.

Preferred among the racemic compounds of Formula (2) are the compounds of Formula (18):

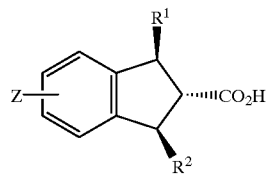

(18)

wherein $R^1$, $R^2$ and Z are as described in Formula (1); or a pharmaceutically acceptable salt thereof.

By the term cyclopentanopyridine derivatives as used herein is meant the racemic compounds of Formula (3):

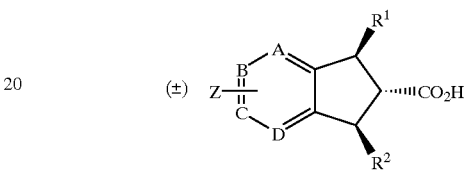

(3)

wherein three of A, B, C and D are carbon atoms and one is a nitrogen atom; and $R^1$, $R^2$ and Z are as described in Formula (1);

or a pharmaceutically acceptable salt thereof.

Preferred among the racemic compounds of Formula (3) are the compounds of Formula (19):

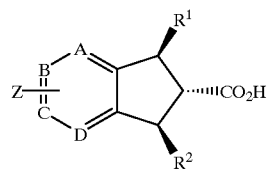

(19)

wherein three of A, B, C and D are carbon atoms and one is a nitrogen atom; and $R^1$, $R^2$ and Z are as described in Formula (1);

or a pharmaceutically acceptable salt thereof.

In Formula (3) compounds, in Formula (19) compounds and in Formula (1) compounds when one of A, B, C or D is a nitrogen atom, preferably A is nitrogen.

Pharmaceutically acceptable salts of the compounds of Formulas (1), (2), (3), (17), (18) and (19) are formed where appropriate by methods well known to those of skill in the art.

Pharmaceutically acceptable salts of (+) (1S, 2R, 3S)-3-[2-2-hydroxyeth-1-yloxy)-4methoxyphenyl]-1-(3,4-methylenedioxyphenyl)-5-(prop-1-yloxy)indane-2-carboxylic acid and (+) (1S, 2R, 3S)-3-(2-carboxymethoxy-4-methoxyphenyl)-1-(3,4-methylenedioxyphenyl)-5-(prop-1-yloxy)indane-2carboxylic acid are formed where appropriate by methods well known to those of skill in the art.

By the term "Pr" as used herein is meant n-propyl.

The term 'activation reaction' for use herein refers to the numerous reactions and reaction conditions well known to those skilled in the art to effect the introduction of a Br, I, —$OSO_2CF_3$ or a —$OSO_2F$ substituent.

By the term 'chiral reduction' as used herein refers to reagents and reaction conditions that effect an enantioselective reduction, preferably using, a chiral catalyst, most preferably using (R)-3,3-diphenyl-1-methyltetrahydro-1H, 3H-pyrrolo-[1,2-c][1.3.2]oxazaborole (as used hereinafter and in the claims (R)-MeCBS which is available from the Callery Chemical Co. of Evans City, Pa.).

The term (+) (1S, 2R, 3S)-3-[2-(2-hydroxyeth-1-yloxy)-4-methoxyphenyl]-1-(3,4-methylenedioxyphenyl)-5-(prop-1-yloxy)indane-2-carboxylic acid as used herein utilizes standard chemical terminology and refers to compound (o)

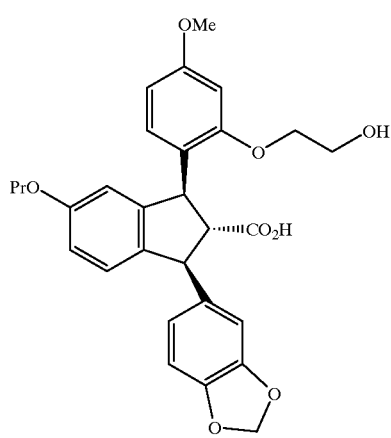

(o)

The term (+) (1S, 2R, 3S)-3-[2-(2-hydroxyeth-1-yloxy)-4-methoxyphenyl]-1-(3,4-methylenedioxyphenyl)-5-(prop-1-yloxy)indane-2-carboxylic acid ethylene diamine salt (2:1) as used herein utilizes standard chemical terminology and refers to Compound (p)

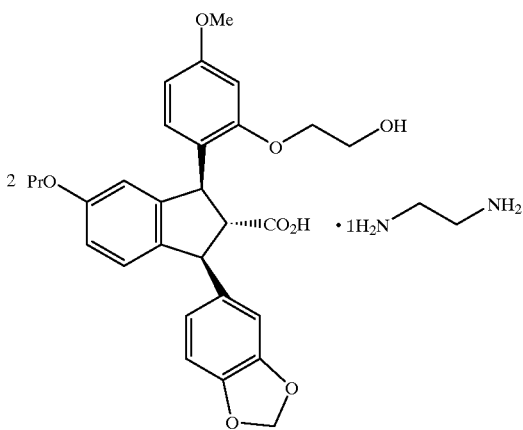

(p)

The term (+) (1S, 2R, 3S)-3-(2-carboxymethoxy-4-methoxyphenyl)-1-(3,4-methylenedioxyphenyl)-5-(prop-1-yloxy)indane-2-carboxylic acid as used herein utilizes standard chemical terminology and refers to compound (k)

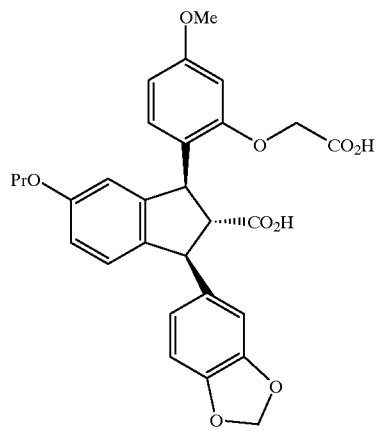

(k)

The term (+) (1S, 2R, 3S)-3-(2-carboxymethoxy-4-methoxyphenyl)-1-(3,4-methylenedioxyphenyl)-5-(prop-1-yloxy)indane-2-carboxylic acid disodium salt as used herein utilizes standard chemical terminology and refers to Compound (1)

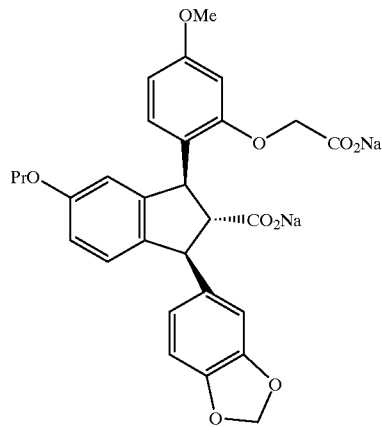

(1)

The indane carboxylates of Formula (18) of the current invention are prepared by methods outlined in the Schemes below and in the Examples from compounds of Formula (a):

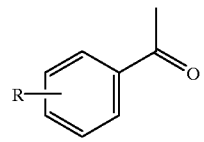

(a)

where R is H, OH, $C_{1-5}$alkoxy (preferably n-PrO) or a protected oxy group, such as benzyloxy. Compounds of Formula (a) are known or can be prepared from readily available starting materials by those skilled in the art.

By the term 'oxy protecting group', 'protected oxy group' and 'protected OH' as used herein, is meant any conventional blocking group in the art such as described in "Pro tective Groups in Organic Synthesis" by Theodora W. Greene, Wiley-Interscience, 1981, New York, provided that such oxy protecting group, protected oxy group or such protected OH do not include moieties that render inoperative the presently invented process. A preferred oxy protecting group for use herein is benzyl. A preferred protected OH or protected oxy group for use herein is benzyloxy. When necessary or desired, the deprotection of the protected oxy or the protected OH is performed on products of the synthetic pathways disclosed or claimed herein or, where appropriate or preferable on certain intermediates in these synthetic pathways.

Further, when necessary or desired, R can be converted to a substituent of Z. Reactions to convert R to Z are performed on products of the synthetic pathways disclosed or claimed herein or, where appropriate or preferable on certain intermediates in the synthetic pathways. For example, hydroxyl groups can be converted into $C_{1-5}$alkoxy groups by alkylation. Protected oxy groups can be deprotected and further reacted to form a substituent of Z.

The present invention provides an improved process for the production of indane carboxylates of Formula (18) as indicated in Schemes 1 and 2 below.

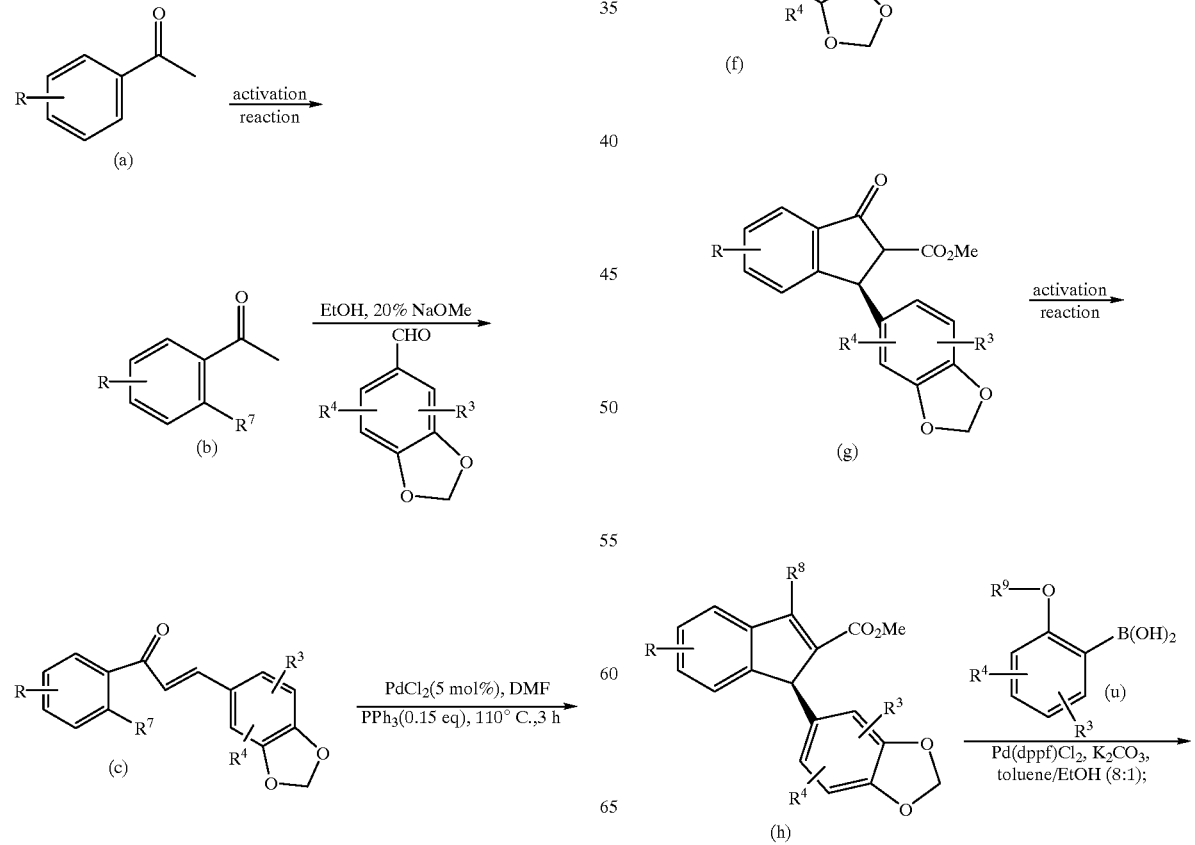

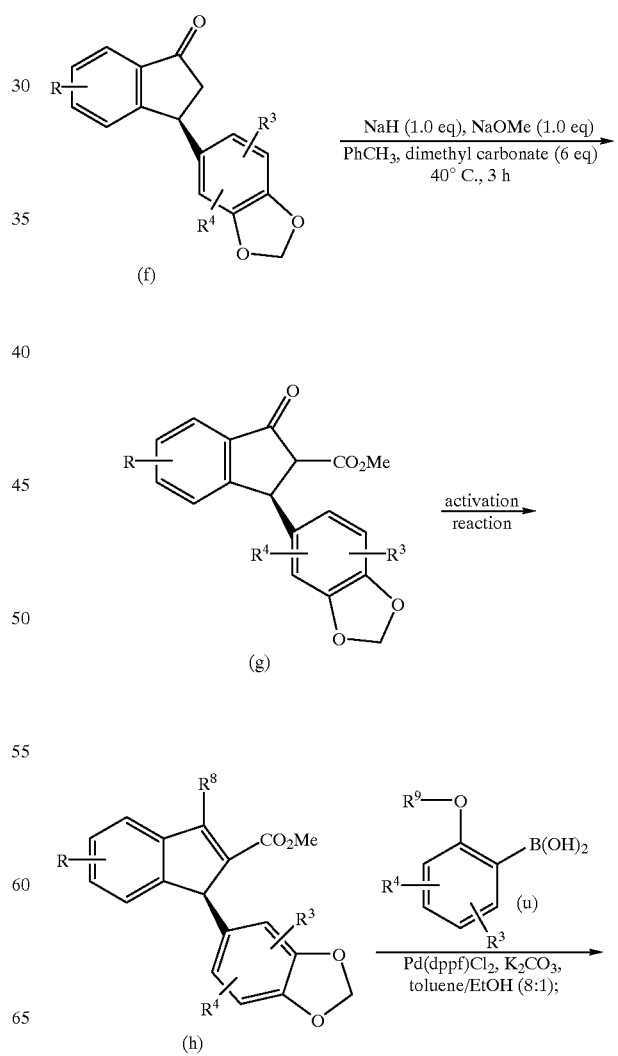

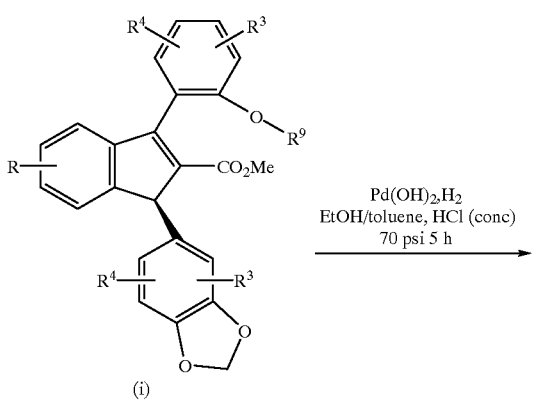

(i)

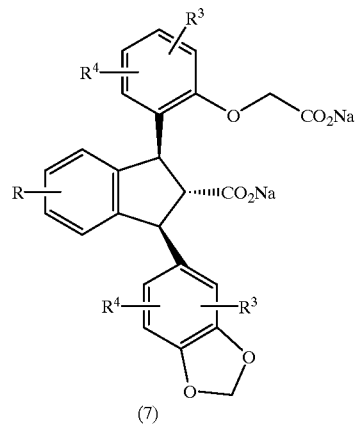

(7)

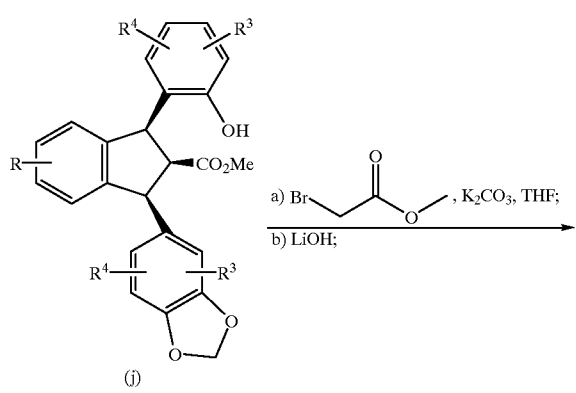

(j)

a) Br-CH₂C(O)O- , K₂CO₃, THF;
b) LiOH;

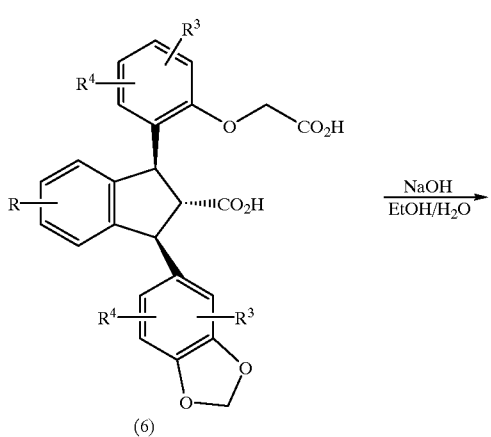

(6)

NaOH / EtOH/H₂O →

Scheme 1 outlines formation of indane carboxylates wherein $R^5$ is —$OCH_2CO_2H$, preferably the disodium salt, Compound (1). As used in Scheme 1, $R^3$ and $R^4$ are as described in Formula (1), R is as described in Formula (a), $R^7$ is Br, 1, —$OSO_2CF_3$ or —$OSO_2F$, and $R^8$ is Br, I, —$OSO_2CF_3$ or —$OSO_2F$ and $R^9$ is an oxy protecting group. Compounds of Formula (b) are prepared in one or more steps by treating a compound of Formula (a) in an activation reaction, preferably with hexamethylenetetramine hydrobromide perbromide, to introduce substituent $R^7$. Compounds of Formula (c) are prepared by treating the compounds of Formula (b) with an appropriately substituted piperonal and sodium methoxide. Compounds of Formula (d) are prepared by treating Formula (c) compounds with a phosphine, preferably triphenylphosphine, a base, preferably potassium carbonate and a palladium catalysts, preferably palladium (II) chloride. Compounds of Formula (d) are treated in a chiral reduction, preferably with a chiral catalyst, most preferably with (R)-3,3-diphenyl-1-methyltetrahydro-1H, 3H-pyrrolo-[1, 2-c][1.3.2]oxazaborole (as used hereinafter and in the claims (R)-MeCBS which is available from the Callery Chemical Co. of Evans City, Pa.), a borane complex, preferably borane-tetrahydrofuran complex, and a base, preferably triethylamine, to give compounds of Formula (e) as the predominately pure enantiomer. Treatment of Formula (e) compounds with a base, such as triethylamine, and a palladium catalyst, such as [1,2-bis(diphenylphosphino) ethane] palladium (H) chloride (as used hereinafter and in the claims Pd(dppe)Cl₂ which is available from the Strem Chemical Co. of Newburyport Ma.) gives compounds of Formula (f) as the predominately pure enantiomer. Treatment of Formula (f) compounds with dimethyl carbonate, sodium hydride and sodium methoxide gives compounds of Formula (g). Compounds of Formula (h) are prepared by treating Formula (g) compounds in an activation reaction, preferably with sodium hydride and fluorosulfonic anhydride, to introduce substituent $R^8$. Compounds of Formula (i) are prepared by the catalytic coupling of Formula (h) compounds and Formula (u) compounds, preferably using [1,1'-bis(diphenylphosphino)ferrocene] palladium (II) chloride (as used hereinafter and in the claims Pd(dppf)Cl₂ which can be purchased from the Strem Chemical Co. of Newburyport, Mass.). Hydrogenation of Formula (i) compounds with a palladium catalyst, preferably palladium hydroxide on carbon, gives compounds of Formula (j). Compounds of Formula (6), preferably Compound (k) as used herein, are prepared by treating Formula (j) compounds with methyl bromoacetate, a base, preferably potassium carbonate, followed by treatment with lithium hydroxide monohydrate or sodium hydroxide and acid workup. Compounds of Formula (6) are treated with sodium hydroxide to give Formula (7) compounds, preferably Compound (1) as used herein.

Scheme 2

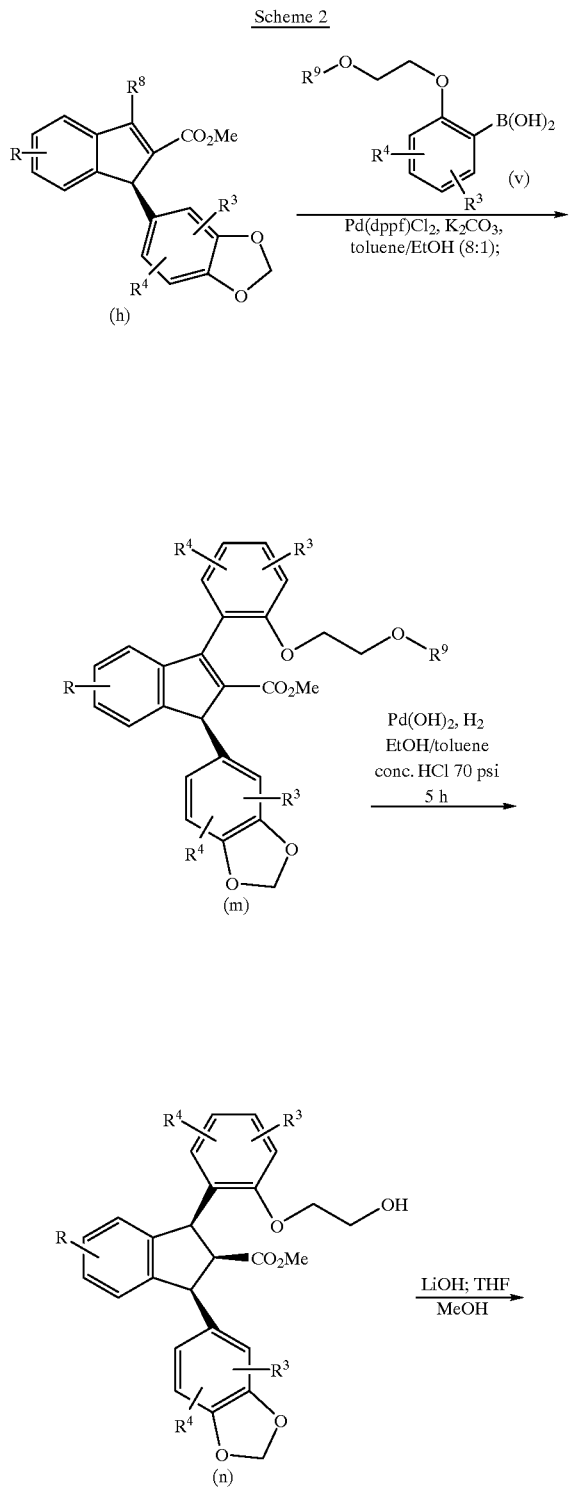

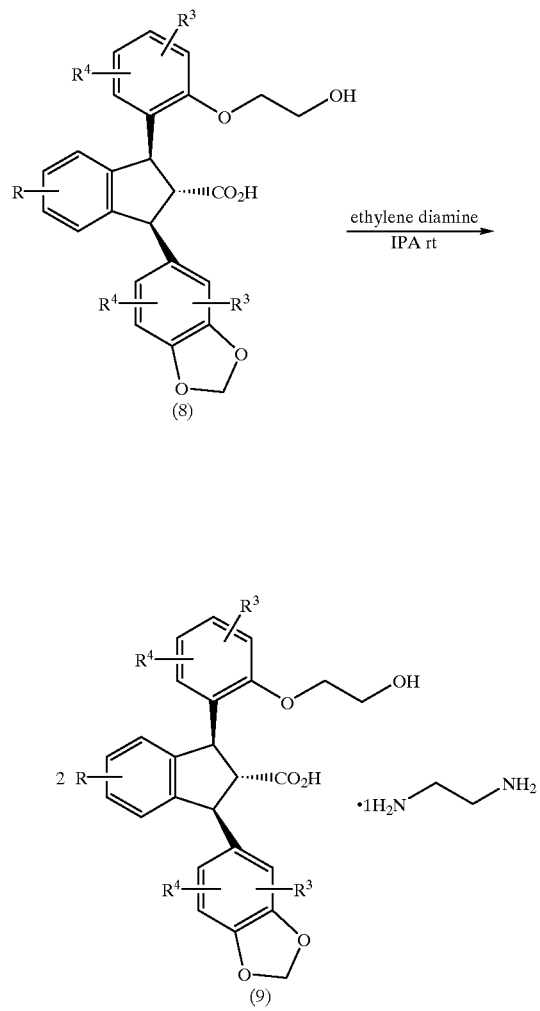

Scheme 2 outlines formation of indane carboxylates wherein $R^5$ is —$OCH_2CH_2OH$, preferably the ethylene diamine salt (2:1), Compound (p). As used in Scheme 2, $R^3$ and $R^4$ are as described in Formula (1), R is as described in Formula (a), $R^7$ is Br, I, —$OSO_2CF_3$ or —$OSO_2F$, $R^8$ is Br, I, —$OSO_2CF_3$ or —$OSO_2F$ and $R^9$ is an oxy protecting group. As used in Scheme 2 a compound of Formula (h) from Scheme 1 is coupled with a compound of Formula (v) using a catalyst, preferably Pd(dppf)Cl$_2$ to give compounds of Formula (m). Hydrogenation of Formula (m) compounds with a palladium catalyst, preferably palladium hydroxide on carbon gives compounds of Formula (n). Compounds of Formula (8), preferably Compound (o) as used herein, are prepared by treating Formula (n) compounds with lithium hydroxide monohydrate. Compounds of Formula (8) are treated with ethylene diamine to give Formula (9) compounds, preferably Compound (p) as used herein.

The racemic compounds of Formulas (1), (2) and (3) are prepared according to the methods outlined in Schemes (1) and (2) and in the Examples by substituting a compound of Formula (10):

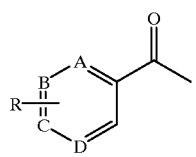

(10)

wherein A, B, C and D are carbon atoms or three of A, B, C and D are carbon atoms and one is a nitrogen atom and R is H, OH, $C_{1-5}$alkoxy (preferably n-PrO) or a protected oxy group, such as benzyloxy, for the compound of Formula (a) and by substituting an achiral reduction, such as using sodium borohydride in methanol, for the chiral reduction used to convert compounds of Formula (d) to compounds of Formula (e) in Scheme 1.

Compounds of Formula (10) are known or can be prepared from readily available starting materials by those skilled in the art.

Thus, an achiral reduction is substituted for the chiral reduction used to convert compounds of Formula (d) to compounds of Formula (e) in Scheme 1 to prepare compounds of Formula (2) and intermediates useful in preparing compounds of Formula (2). The compounds of Formula (10) are utilized in Scheme 1, by substituting an achiral reduction for the chiral reduction used to convert compounds of Formula (d) to compounds of Formula (e) in Scheme 1, to prepare compounds of Formula (1) and intermediates useful in preparing compounds of Formula (1). The compounds of Formula (10), wherein three of A, B, C and D are carbon atoms and one is a nitrogen atom, are utilized in Scheme 1, by substituting an achiral reduction for the chiral reduction used to convert compounds of Formula (d) to compounds of Formula (e) in Scheme 1, to prepare compounds of Formula (3) and intermediates useful in preparing compounds of formula (3).

The cyclopentano[b]pyridine derivatives of Formula (19) of the current invention are prepared according the methods outlined in Schemes 1 and 2 and in the Examples from compounds of Formula (10) wherein three of A, B, C and D are carbon atoms and one is a nitrogen atom. Preferred among Formula (10) compounds when a nitrogen is present are those wherein A is nitrogen.

The aromatic ring-fused cyclopentane derivatives of Formula (17) of the current invention are prepared according the methods outlined in Schemes 1 and 2 and in the Examples from compounds of Formula (10) wherein A, B, C and D are carbon atoms or three of A, B, C and D are carbon atoms and one is a nitrogen atom. Preferred among Formula (10) compounds when a nitrogen is present are those wherein A is nitrogen.

Prepared in synthesizing the indane carboxylates of Formula (18), preferably Compound (1) and Compound (p), are novel intermediates of Formula (b):

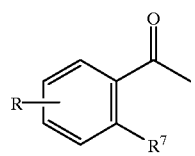

(b)

where R is as described in Formula (a) and $R^7$ is Br, I, $-OSO_2CF_3$ or $-OSO_2F$.

Also prepared in synthesizing the indane carboxylates of Formula (18), preferably Compound (1) and Compound (p), are novel intermediates of Formula (c):

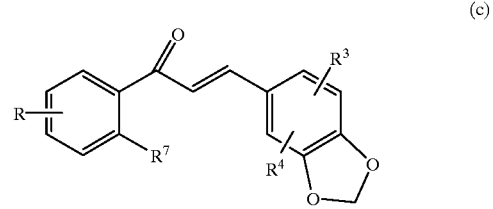

(c)

where $R^3$ and $R^4$ as described in Formula (1), R is as described in Formula (a), and $R^7$ is Br, I, $-OSO_2CF_3$ or $-OSO_2F$.

Also prepared in synthesizing the indane carboxylates of Formula (18), preferably Compound (1) and Compound (p), are novel intermediates of Formula (d):

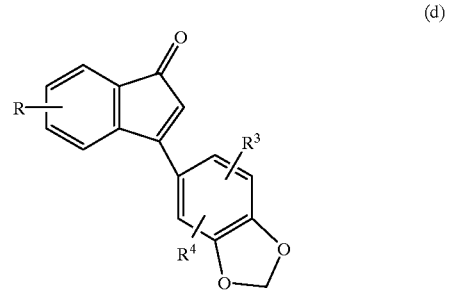

(d)

where $R^3$ and $R^4$ are as described in Formula (1) and R is as described in Formula (a).

Also prepared in synthesizing the indane carboxylates of Formula (18), preferably Compound (1) and Compound (p), are novel intermediates of Formula (e):

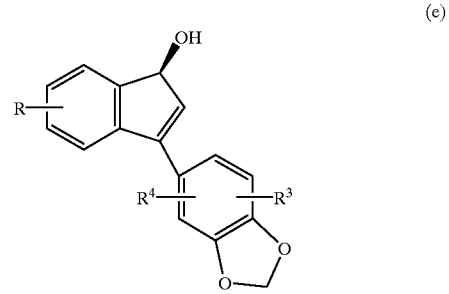

(e)

where $R^3$ and $R^4$ are as described in Formula (1) and R is as described in Formula (a).

Also prepared in synthesizing the indane carboxylates of Formula (18), preferably Compound (1) and Compound (p), are novel intermediates of Formula (f):

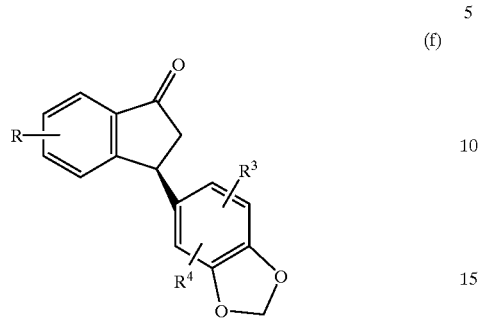

(f)

where $R^3$ and $R^4$ are as described in Formula (1) and R is as described in Formula (a).

Also prepared in synthesizing the indane carboxylates of Formula (18), preferably Compound (1) and Compound (p), are novel intermediates of Formula (g):

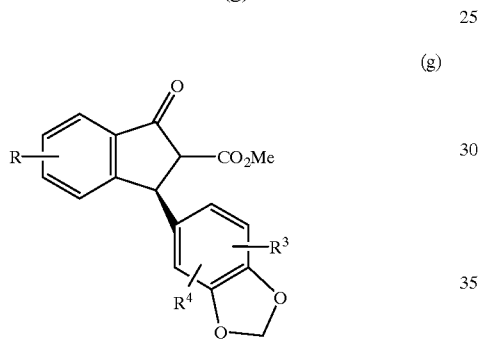

(g)

where $R^3$ and $R^4$ are as described in Formula (1) and R is as described in Formula (a).

Also prepared in synthesizing the indane carboxylates of Formula (18), preferably Compound (1) and Compound (p), are novel intermediates of Formula (h):

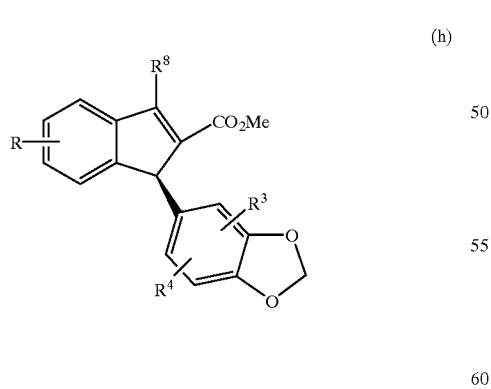

(h)

where $R^3$ and $R^4$ are as described in Formula (1), R is as described in Formula (a) and $R^8$ is Br, I, —$OSO_2CF_3$ or —$OSO_2F$.

Also prepared in synthesizing the indane carboxylates of Formula (18), preferably Compound (1), are novel intermediates of Formula (i):

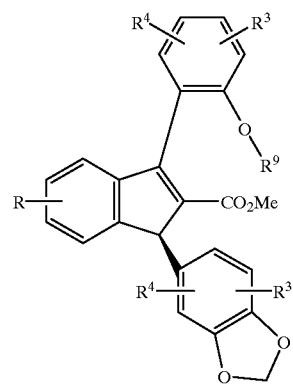

(i)

where $R^3$ and $R^4$ are as described in Formula (1), R is as described in Formula (a) and $R^9$ is an oxy protecting group.

Also prepared in synthesizing the indane carboxylates of Formula (18), preferably Compound (1), are novel intermediates of Formula (j):

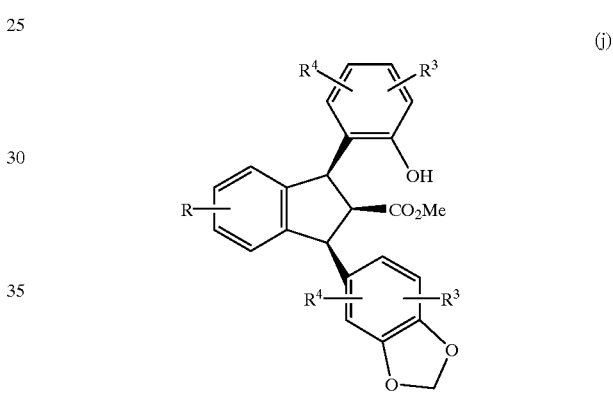

(j)

where $R^3$ and $R^4$ are as described in Formula (1) and R is as described in Formula (a).

Also prepared in synthesizing the indane carboxylates of Formula (18), preferably Compound (p), are novel intermediates of Formula (m):

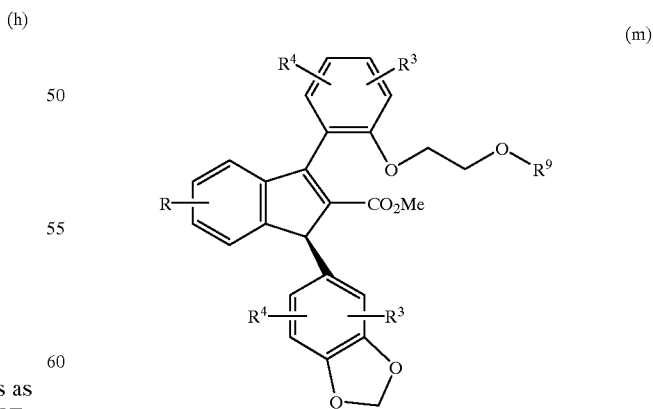

(m)

where $R^3$ and $R^4$ are as described in Formula (1), R is as described in Formula (a) and $R^9$ is an oxy protecting group.

Also prepared in synthesizing the indane carboxylates of Formula (18), preferably Compound (p), are novel intermediates of Formula (n):

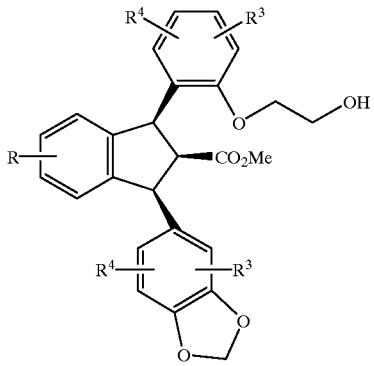

(n)

where $R^3$ and $R^4$ are as described in Formula (1) and R is as described in Formula (a).

Prepared in synthesizing the aromatic ring-fused cyclopentane derivatives of Formula (1) are novel intermediates of Formula (10):

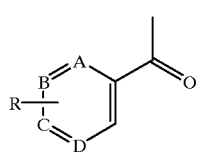

(10)

wherein A, B, C and D are carbon atoms or three of A, B, C and D are carbon atoms and one is a nitrogen atom and R is as described in Formula (a).

Prepared in synthesizing the cyclopentanopyridine derivatives of Formula (19) are intermediates of Formula (10) where three of A, B, C and D are carbon atoms and one is a nitrogen atom and R is as described in Formula (a).

Also prepared in synthesizing the aromatic ring-fused cyclopentane derivatives of Formula (1) are novel intermediates of Formula (11):

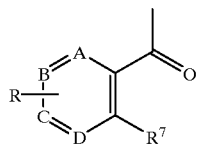

(11)

wherein A, B, C and D are carbon atoms or three of A, B, C and D are carbon atoms and one is a nitrogen atom, R is as described in Formula (a) and $R^7$ is Br, I, —$OSO_2CF_3$ or —$OSO_2F$.

Also prepared in synthesizing the cyclopentanopyridine derivatives of Formula (19) are intermediates of Formula (11) where three of A, B, C and D are carbon atoms and one is a nitrogen atom, R is as described in Formula (a) and $R^7$ is Br, I, —$OSO_2CF_3$ or —$OSO_2F$.

Also prepared in synthesizing the aromatic ring-fused cyclopentane derivatives of Formula (1) are novel intermediates of Formula (12):

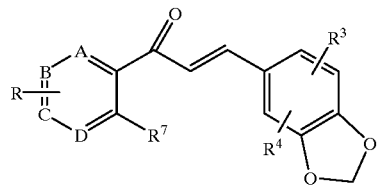

(12)

wherein A, B, C and D are carbon atoms or three of A, B, C and D are carbon atoms and one is a nitrogen atom, R is as described in Formula (a) and $R^7$ is Br, I, —$OSO_2CF_3$ or —$OSO_2F$.

Also prepared in synthesizing the cyclopentanopyridine derivatives of Formula (19) are intermediates of Formula (12) where three of A, B, C and D are carbon atoms and one is a nitrogen atom, R is as described in Formula (a) and $R^7$ is Br, I, —$OSO_2CF_3$ or —$OSO_2F$.

Also prepared in synthesizing the aromatic ring-fused cyclopentane derivatives of Formula (1) are novel intermediates of Formula (13):

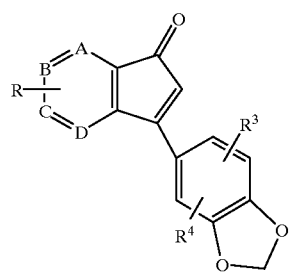

(13)

wherein A, B, C and D are carbon atoms or three of A, B, C and D are carbon atoms and one is a nitrogen atom, R is as described in Formula (a) and $R^7$ is Br, I, —$OSO_2CF_3$ or —$OSO_2F$.

Also prepared in synthesizing the cyclopentanopyridine derivatives of Formula (19) are intermediates of Formula (13) where three of A, B, C and D are carbon atoms and one is a nitrogen atom, R is as described in Formula (a) and $R^7$ is Br, I, —$OSO_2CF_3$ or —$OSO_2F$.

Also prepared in synthesizing the cyclopentanopyridine derivatives of Formula (3) are the novel racemic intermediates of Formula (14):

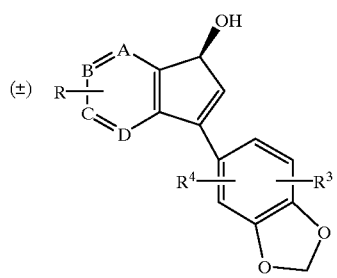

(14)

wherein three of A, B, C and D are carbon atoms and one is a nitrogen atom, R is as described in Formula (a) and $R^3$ and $R^4$ are as described in Formula (1).

Also prepared in synthesizing the cyclopentanopyridine derivatives of Formula (19) are the novel intermediates of Formula (15):

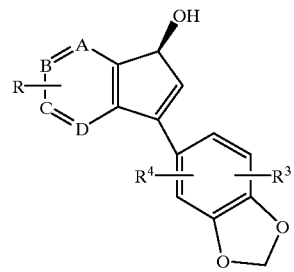
(15)

wherein three of A, B, C and D are carbon atoms and one is a nitrogen atom, R is as described in Formula (a) and $R^3$ and $R^4$ are as described in Formula (1).

Also prepared in synthesizing the cyclopentanopyridine derivatives of Formula (3) are the novel racemic intermediates of Formula (16):

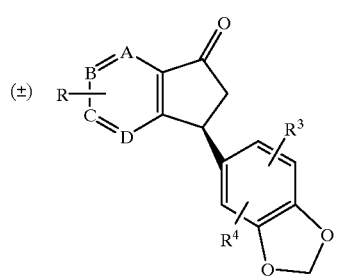
(16)

wherein three of A, B, C and D are carbon atoms and one is a nitrogen atom, R is as described in Formula (a) and $R^3$ and $R^4$ are as described in Formula (1).

Also prepared in synthesizing the cyclopentanopyridine derivatives of Formula (19) are the novel intermediates of Formula (20):

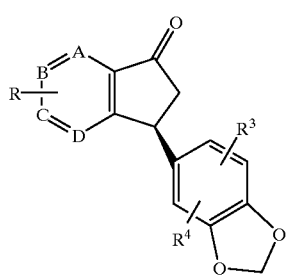
(20)

wherein three of A, B, C and D are carbon atoms and one is a nitrogen atom, R is as described in Formula (a) and $R^3$ and $R^4$ are as described in Formula (1).

Also prepared in synthesizing the cyclopentanopyridine derivatives of Formula (3) are the novel racemic intermediates of Formula (21):

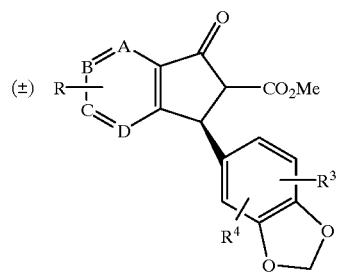
(21)

wherein three of A, B, C and D are carbon atoms and one is a nitrogen atom, R is as described in Formula (a) and $R^3$ and $R^4$ are as described in Formula (1).

Also prepared in synthesizing the cyclopentanopyridine derivatives of Formula (19) are the novel intermediates of Formula (22):

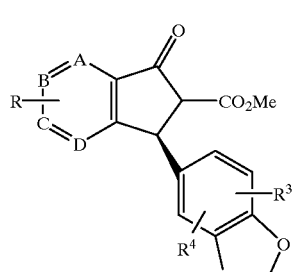
(22)

wherein three of A, B, C and D are carbon atoms and one is a nitrogen atom, R is as described in Formula (a) and $R^3$ and $R^4$ are as described in Formula (1).

Also prepared in synthesizing the cyclopentanopyridine derivatives of Formula (3) are the novel racemic intermediates of Formula (23):

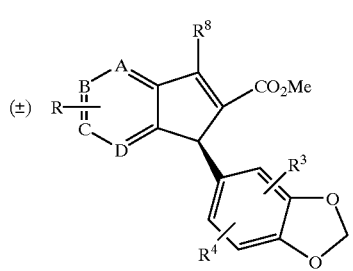
(23)

wherein three of A, B, C and D are carbon atoms and one is a nitrogen atom, $R^3$ and $R^4$ are as described in Formula (1), R is as described in Formula (a) and $R^8$ is Br, I, —$OSO_2CF_3$ or —$OSO_2F$.

Also prepared in synthesizing the cyclopentanopyridine derivatives of Formula (19) are the novel intermediates of Formula (24):

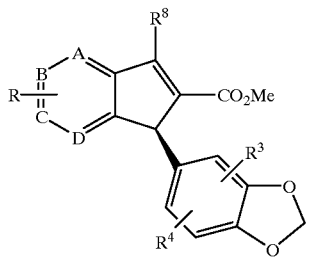

(24)

wherein three of A, B, C and D are carbon atoms and one is a nitrogen atom, $R^3$ and $R^4$ are as described in Formula (1), R is as described in Formula (a) and $R^8$ is Br, I, —OSO$_2$CF$_3$ or —OSO$_2$F.

Also prepared in synthesizing the cyclopentanopyridine derivatives of Formula (3) are the novel racemic intermediates of Formula (25):

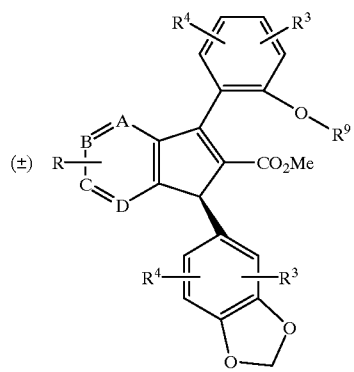

(25)

wherein three of A, B, C and D are carbon atoms and one is a nitrogen atom, R is as described in Formula (a), $R^3$ and $R^4$ are as described in Formula (1) and $R^9$ is an oxy protecting group.

Also prepared in synthesizing the cyclopentanopyridine derivatives of Formula (19) are the novel intermediates of Formula (26):

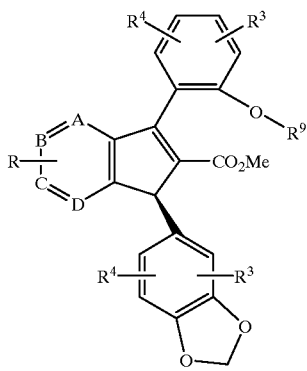

(26)

wherein three of A, B, C and D are carbon atoms and one is a nitrogen atom, R is as described in Formula (a), $R^3$ and $R^4$ are as described in Formula (1) and $R^9$ is an oxy protecting group.

Also prepared in synthesizing the cyclopentanopyridine derivatives of Formula (3) are the novel racemic intermediates of Formula (27):

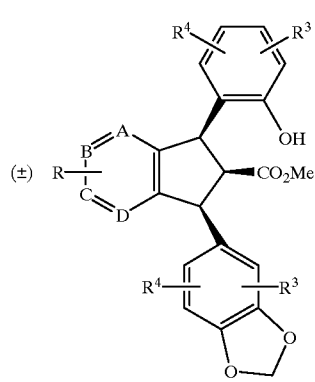

(27)

wherein three of A, B, C and D are carbon atoms and one is a nitrogen atom, R is as described in Formula (a) and $R^3$ and $R^4$ are as described in Formula (1).

Also prepared in synthesizing the cyclopentanopyridine derivatives of Formula (19) are the novel intermediates of Formula (28):

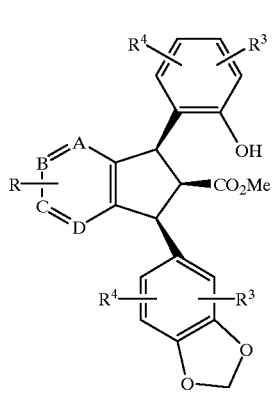

(28)

wherein three of A, B, C and D are carbon atoms and one is a nitrogen atom, R is as described in Formula (a) and $R^3$ and $R^4$ are as described in Formula (1).

Also prepared in synthesizing the cyclopentanopyridine derivatives of Formula (3) are the novel racemic intermediates of Formula (29):

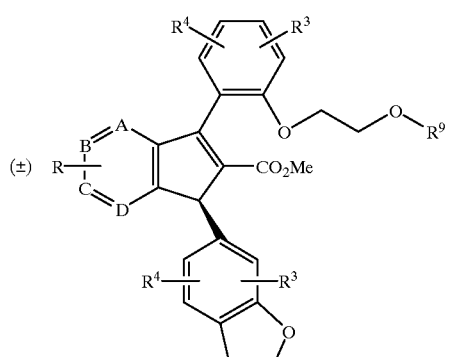

(29)

wherein three of A, B, C and D are carbon atoms and one is a nitrogen atom, R is as described in Formula (a), $R^3$ and $R^4$ are as described in Formula (1) and $R^9$ is an oxy protecting group.

Also prepared in synthesizing the cyclopentanopyridine derivatives of Formula (19) are the novel intermediates of Formula (30):

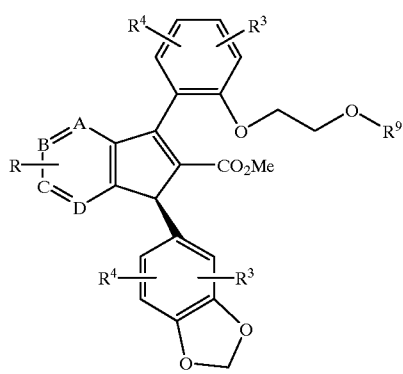

(30)

wherein three of A, B, C and D are carbon atoms and one is a nitrogen atom, R is as described in Formula (a), $R^3$ and $R^4$ are as described in Formula (1) and $R^9$ is an oxy protecting group.

Also prepared in synthesizing the cyclopentanopyridine derivatives of Formula (3) are the novel racemic intermediates of Formula (31):

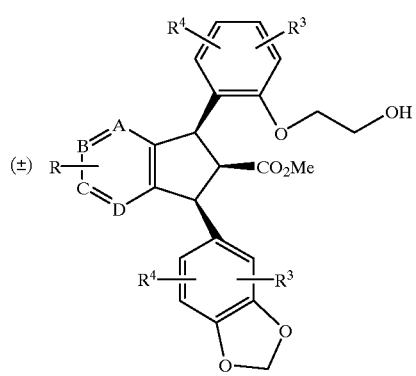

(31)

wherein three of A, B, C and D are carbon atoms and one is a nitrogen atom, R is as described in Formula (a) and $R^3$ and $R^4$ are as described in Formula (1).

Also prepared in synthesizing the cyclopentanopyridine derivatives of Formula (19) are the novel intermediates of Formula (32):

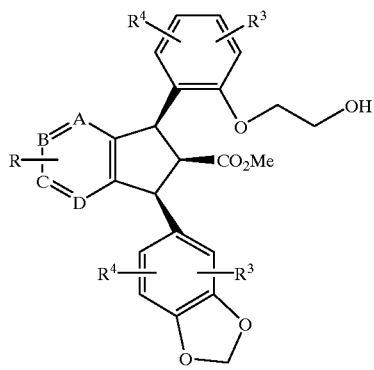

(32)

wherein three of A, B, C and D are carbon atoms and one is a nitrogen atom, R is as described in Formula (a) and $R^3$ and $R^4$ are as described in Formula (1).

All of the starting materials and reagents used herein are known and readily available or can be easily made from known and readily available reagents.

For example, compounds of Formula (u) are prepared according to the following steps:

a) treating a compound of the formula

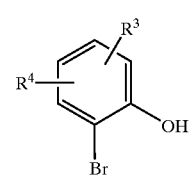

(bb)

where $R^3$ and $R^4$ are as described in Formula (1), in a reaction to convert the OH to a protected oxy group, such as benzyl bromide and sodium hydride in N,N-dimethylformamide, to form the compound

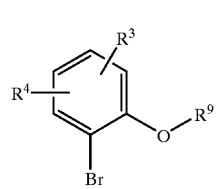

(aa)

where $R^3$ and $R^4$ are as described in Formula (1) and $R^9$ is an oxy protecting group, b) treating the product of step a) with magnesium turnings, 1,2-dibromoethane and trimethylborate (B(OMe)$_3$) in tetrahydrofuran to form compounds of Formula (u)

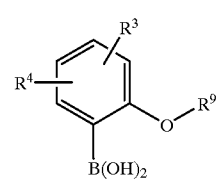

(u)

where $R^3$ and $R^4$ are as described in Formula (1) and $R^9$ is an oxy protecting group.

For example, compounds of Formula (v) are prepared according to the following steps:

a) treating a compound of the formula

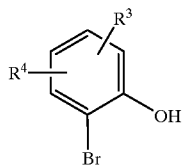
(bb)

where $R^3$ and $R^4$ are as described in Formula (1), with benzyloxyethyl bromide or another suitable protected oxy group, a base, such as potassium carbonate, to form compounds of Formula (ab)

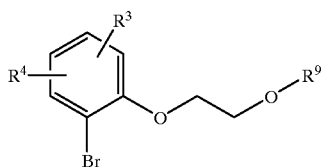
(ab)

where $R^3$ and $R^4$ are as described in Formula (I) and $R^9$ is an oxy protecting group, b) treating the product of step a) with magnesium turnings, 1,2-dibromoethane and trimethylborate (B(OMe)₃) in tetrahydrofuran to form compounds of Formula (v)

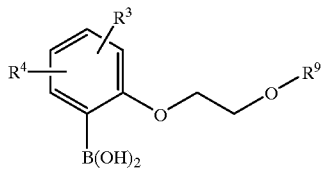
(v)

where $R^3$ and $R^4$ are as described in Formula (1) and $R^9$ is an oxy protecting group.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXAMPLES

Example 1

Corresponding to Scheme 1

(+) (1S, 2R, 3S)-3-(2-Carboxymethoxy-4-methoxyphenyl)-1-(3,4-methylenedioxyphenyl)-5-(prop-1-yloxy)indane-2-carboxylic acid disodium salt (i). 1-(2-Bromo-5-propoxyphenyl)ethanone (a compound of Formula (b))

A 3 L three-necked flask equipped with mechanical stirrer was charged with CH₃CN (200 mL), deionized H₂O (900 mL) and 3-(prop-1-yloxy)acetophenone (125 g, 0.7 mol). To this biphasic mixture was added hexamethylenetetramine hydrobromide perbromide (348 g, 0.913 mol) forming a heterogeneous mixture which was stirred at ambient temperature for 18 h. The mixture was then diluted with EtOAc (700 mL), the organic phase separated, washed with brine (500 mL), dried (MgSO₄) and concentrated in vacuo to afford 1-(2-Bromo-5-propoxyphenyl)ethanone as a yellow solid (176.4 g, 98%); A recrystallization from boiling hexane (230 mL) affords 1-(2-Bromo-5-propoxyphenyl)ethanone as a white solid (139 g, 77%): mp 50.0–52.0° C.; $^1$H NMR δ7.4 (d, J=8.8 Hz, 1H), 6.95 (d, J=3.0 Hz, 1H), 6.85 (dd, J=3.0, 8.8 Hz, 1H), 3.9 (t, J=6.5 Hz, 2H), 2.6 (s, 3H), 1.8 (quintet, J=7.8 Hz, 2H), 1.05 (t, J=7.4 Hz, 3H).

(ii). 3-(1,3-Benzodioxol-5-yl)-1-(2-bromo-5-propoxyphenyl)-2-propen-1-one (a compound of Formula (c))

A 1 L three-necked flask equipped with mechanical stirrer was charged with EtOH (300 miL), piperonal (19.3 g, 0.128 mol) and 1-(2-Bromo-5-propoxyphenyl)ethanone (33.0 g, 0.128 mol). Sodium methoxide (29 mL, 25% in MeOH, 0.134 mol) was then added and the solution stirred at ambient temperature. After 4h, a yellow precipitate had formed which was filtered, washed with cold EtOH (2×50 mL), and air-dried affording 3-(1,3-benzodioxol-5-yl)-1-(2-bromo-5-propoxyphenyl)-2-propen-1-one as a yellow solid (42.7 g, 86%); mp 80.0–82.0° C. $^1$H NMR δ7.55 (d, J=8.7 Hz, 1H), 7.4 (d,J=16.0 Hz, 1H), 7.1 (d,J=1.2 Hz, 1H), 7.0 (d,J=8.1 Hz, 1H), 7.0–6.8 (m, 4H), 6.05 (s, 2H), 3.95 (t, J=6.5 Hz, 2H), 1.8 (quintet, J=7.8 Hz, 2H), 1.05 (t, J=7.4 Hz, 3H).

(i) and (ii) can be combined as follows.

A 3 L three-necked flask equipped with air-driven mechanical stirrer, thermometer and 125 mL addition funnel was charged with hexamethylenetetramine (90.6 g, 0.65 mol) and deionized H₂O (757 mL). The flask was cooled to 15° C., a 48% HBr solution (73 mL, 0.65 mol) added over 5 minutes to form a clear colorless solution followed by the addition of bromine (33.3 mL, 0.65 mole) over ten minutes while maintaining the temperature below 20° C. Stir the mixture for 1 hour and add a solution of 3-(prop-1-yloxy) acetophenone (100 g, 0.56 mol) in CH₃CN (157 mL) and stir for 1–2 hours at room temperature. Add t-BuOMe (430 mL), remove aqueous phase and wash organic phase with 5% NaHCO₃ solution (125 mL), H₂O (215 mL) and 20% NaCl solution (145 mL). Transfer the organic phase to a 3 L 3-necked flask equipped with air driven stirrer, simple distillation apparatus, and 125 mL addition funnel. Remove solvent to ¼ volume by distillation at atmospheric pressure and add EtOH (500 mL, 190 proof). Continue distillation at atmospheric pressure until the vapor temperature is 76° C. Cool solution to 15° C and charge with EtOH (1.3 L) and piperonal (83.8 g, 0.56 mol). Add 25% NaOMe solution (119 mL, 0.56 mol) dropwise over 20 minutes and stir vigorously for 2 h at room temperature. Filter yellow precipitate, rinse filter cake with EtOH (2×140 mL) and dry to a constant weight (177 g, 81% yield): mp 80.0–82.0° C.

(iii). 3-(1,3-Benzodioxol-5-yl)-6-propoxy-1H-inden-1-one (a compound of Formula (d))

A 1 L three-necked flask equipped with mechanical stirrer was charged with DMF (190 mL), PPh₃ (960 mg, 3.66 mmol), K₂CO₃ (9 g, 65 mmol) and 3-(1,3-benzodioxol-5-yl)-1-(2-bromo-5-propoxyphenyl)-2-propen-1-one (10 g, 26 mmol). Upon purging the solution with nitrogen, PdCl₂ (230 mg., 1.3 mmol.) was added and the mixture heated to 110° C. After 1.8 h, the hot solution was poured into ice water (100 mL) and diluted with EtOAc (250 mL). The aqueous phase was back-extracted with EtOAc (150 mL) and the organic layers combined, washed with brine (200 mL), dried (MgSO₄) and concentrated to afford a red oil (9.65 g). The oil was dissolved in EtOAc/hexane (1:2, 150 mL), filtered through SiO₂ (156 g) and the filtrate concentrated to give a red semi-solid (6.9 g). The solid was recrystallized from MeOH (100 mL) affording 3-(1,3-benzodioxol-5-yl)-6-propoxy-1H-inden-1-one as an orange solid in two crops (67%): 4.0 g, mp 90.0–93.0° C; 1.3 g, mp 92.0–94.0° C.

(iii)a. 3-(1,3-Benzodioxol-5-yl)-6-propoxy-1H-inden-1-one

A 1 L three-necked flask equipped with mechanical stirrer was charged with DMF (1.5 L), PPh₃ (3.6 g, 13.7 mmol), K₂CO₃ (67.5 g, 0.489 mol), PdCl₂ (0.855 g, 4.82 mmol) and 3-(1,3-Benzodioxol-5-yl)-1-(2-bromo-5-propoxyphenyl)-2-propen-1-one (75 g, 0.193 mol). Upon purging the solution with nitrogen, heat the mixture at 110 ° C. for 0.5 h, cool to 40° C.,concentrate to ½ volume (57° C., 40 mm Hg), and add H₂O (750 ml) and stir the reaction mixture at room temperature for 1 h. Filter the precipitate and wash with H₂O (500 mL). Transfer the wet solid (62 g) to a 1 L 3-necked flask, add EtOAc (500 ml) and 20% KSCN solution (250 mL) and heat the biphasic mixture to 65° C. for 1 h. Remove the aqueous layer, wash the organic layer with brine (2×250 mL), dry over MgSO₄ and concentrate in vacuo. Slurry the crude solid in iPrOAc/iPrOH (200 ml, 1:1) and stir for 1.5 h at 5° C. Filter the product, wash with cold iPrOH (50 ml, 0° C.) and air dry to afford 3-(1,3-Benzodioxol-5-yl)-6-propoxy-1H-inden-1-one as an orange solid (43 g, 73% yield): mp 99.0–101.0° C.; ¹H NMR δ7.3–7.2 (m, 3H), 7.1 (m, 2H), 6.9 (d, J=8.1 Hz, 1H), 6.75 (dd, J=2.5 8.2 Hz, 1H), 6.05 (s, 1H), 5.8 (s, 1H), 3.95 (t, J=6.6 Hz, 2H), 1.8 (quintet, Hz, 2H), 1.05 (t, J=7.4 Hz, 3H).

(iv). (S)-3-(1,3-Benzodioxol-5-yl)-6-propoxy-1H-inden-1-ol (a compound of Formula (e))

A 100 ml three-necked flask was charged with anhydrous THF (20 mL), (R) -MeCBS catalyst (0.325 mL, 1 M, 0.325 mmol), and BH₃-THF (6.49 mL, 1M, 6.49 mmol) under nitrogen. The solution was cooled to −10° C. and 3-(1,3-benzodioxol-5 yl)-6-propoxy-1H-inden-1-one (2.0 g, 6.49 mmol) in anhydrous THF (20 mL) was added dropwise over 2 h period. After 45 minutes a solution of Et₃N (2.0 mL, 14.3 mmol) and MeOH (1.3 mL, 19.5 mmol) was added cautiously while maintaining the internal temperature below −5° C. The reaction mixture was concentrated in vacuo and purified via flash chromatography (EtOAc/hexane, 1:3) affording (S)-3-(1,3-benzodioxol-5-yl)-6-propoxy-1H-inden-1-ol as a yellow oil (1.9 g, 95%, 94% e.e.); Chiralcel OC column (90:10 IPA/hexane, 2 mL/min, 254 nm): 13.321 min (2.34%) :16.031 min (85.23%); ¹H NMR (CDCl₃) δ7.30 (d, J=8.3 Hz, 1H), 7.2 (s, 1H), 7.1–7.0 (m, 2H), 6.9 (d, J=8.0 Hz, 1H), 6.8 (dd, J=8.4, 2.4 Hz, 1H), 6.25 H), 6.0 (s, 2H), 5.2 (d, J=7.2 Hz, 1H), 3.95 (t, J=6.6 Hz, 3H), 1.85 (m, 2H), 1.0 (t, J=, 3H).

(v). (S)-3-(1,3-Benzodioxol-5-yl)-2,3-dihydro-6-propoxy-1H-inden-1-one (a compound of Formula (f))

A 100 mL three-necked flask was charged with (S)-3-(1, 3-benzodioxol-5-yl)-6-propoxy-1H-inden-1-ol (1.9 g, 6.13 mmol), anhydrous THF (40 mL), Et₃N (2.0 mL, 14.4 mmol) and Pd(dppe)Cl₂ (130 mg, 0.227 mmol) under nitrogen. The mixture was warmed to 40° C. and after 6 h, cooled to room temperature, diluted with EtOAc/hexane solution (1:3, 60 mL) and filtered through SiO₂. The filtrate was concentrated in vacuo affording (S)-3-(1,3-Benzodioxol-5-yl)-2,3-dihydro-6-propoxy-1H-inden-1-one as a yellow solid (1.85 g, 95%, 94% e.e.); mp 63.0–65.0 ° C.; Chiralpak AD column (93:7 IPA/hexane, 1 mL/min, 254 nm): 14.107 min (90.11%), 15.805 min (2.90%).¹H NMR δ7.25–7.1 (m, 3H), 6.75 (d, J=7.9 Hz, 1H), 6.6 (dd, J=1.7, 8.0 Hz, 1H), 6.5 (d, J=1.7 Hz, 1H), 5.9 (s, 2H), 4.4 (dd,J=3.5, 7.8 Hz, 1H), 3.95 (t, J=6.5 Hz, 2H), 3.2 (dd, J=7.8, 19.3 Hz, 1H), 2.6 (dd, J=3.5, 19.1 Hz, 1H), 1.8 (quintet, J=7.8 Hz, 2H), 1.01 (t, J=7.4 Hz, 3H).

(iv) and (v) can be combined as follows.

A 250 mL three-necked flask equipped with air driven stirrer and 250 mL addition funnel was charged with anhydrous THF (50 mL) and (R)-MeCBS (1.6 mL, 1 M, 1.6 mmol). The solution was cooled to −15° C. and BH₃-THF (32.4 mL, 1 M, 32.4 mmol) added in a steady stream. Charge the 250 mL addition funnel with 3-(1,3-Benzodioxol-5-yl)-6-propoxy-1H-inden-1-one (10 g, 32.4 mmol) and anhydrous THF (50 mL) and add the solution dropwise over 1.5 h period while maintaining the internal reaction temperature between −10 to −15° C. Upon complete addition, stir the reaction mixture for 0.5 h at −15° C., cool the solution to −25° C. and add CH₃OH (20 mL) dropwise over 20 minutes while maintaining the internal reaction temperature below −15° C. Warm the solution to 20° C. over 0.5 h and stir the solution for an additional 0.5 h at ambient temperature. Cool the solution to 0° C. and add Et₃N (1 mL, 81 mmol) to the reaction mixture dropwise over 15 minutes while maintaining the internal reaction temperature below 5° C. Add 1,1-bis(triphenylphosphine) nickel(II) chloride (211 mg, 3.24 mmol) and warm the reaction mixture to 60° C. for 4 h. Concentrate the solution to 1/4 volume, cool to room temperature, add Celite (12 g) and then hexanes (85 ml). Stir the mixture vigorously for 10 min and filter through a SiO₂ (10 g) and Celite (10 g) pad. Wash the filter pad with THF/hexane (45 mL/120 mL), combine the filtrates, and transfer to a 500 mL round-bottomed flask. Concentrate the solution in vacuo until a precipitate forms, add hexane (40 mL) and cool the solution to −15 CC for 8 h. Filter the precipitate, wash the filter cake with cold (0° C.) hexane solution and dry under vacuum to afford (S)-3-(1,3-Benzodioxol-5-yl)-2,3-dihydro-6-propoxy-1H-inden-1-one as a light yellow solid (8.1 g, 81%, 88% e.e.): mp 68.0–69.5° C.

(vi). (1S-trans)-Methyl 1-(1,3-benzodioxol-5-yl)-2,3-dihydro-3-oxo-5-propoxy -1H-indene-2-carboxylate (a compound of Formula (g))

A 100 mL three-necked flask under nitrogen was charged with (S)-3-(1,3-Benzodioxol-5-yl)-2,3-dihydro-6-propoxy-1H-inden-1-one (1.5 g, 4.84 mmol), toluene (20 mL), 60% NaH suspension (213 mg, 5.3 mmol), NaOMe (288 mg, 5.3 =mmol), and dimethyl carbonate (2.5 mL, 29 mmol). The solution was warmed to 40 ° C. for 3 h, cooled to 0° C., quenched with 3 M AcOH (0.5 mL) and diluted with H₂O (50 mL) and EtOAc (50 mL). The organic phase was washed with brine (50 mL), dried (MgSO₄) and concentrated. The crude material was triturated with EtOAc/hexane (1:3, 50 mL) affording (1S-trans)-methyl 1-(1,3-benzodioxol-5-yl)-2,3-dihydro-3-oxo-5-propoxy-1H-indene-2-carboxylate as a pale yellow solid (710 mg, 73% yield).

(vi)a. (1S-trans)-Methyl 1-(1,3-benzodioxol-5-yl)-2,3-dihydro-3-oxo-5-propoxy -1H-indene-2-carboxylate A 250 mL three-necked flask under nitrogen was charged with (S)-3-(1,3-Benzodioxol-5-yl)-2,3-dihydro-6-propoxy-1H-inden-1-one (6.6 g, 21.3 mmol, 90% e.e.) and dimethyl carbonate (70 mL). To the solution was added sodium t-amylate (4.7 g, 42.5 mmol) in four portions over 20 minutes to maintain the temperature below 35° C. Upon complete addition of base, stir the solution until the temperature drops to 20° C. (~1.5 h). Cool the solution to 0° C. and add a 50% acetic acid solution (50 mL) over 15 minutes to keep the temperature below 5° C. Concentrate the solution to ¼ volume, add toluene (100 mL), wash the organic phase with water (2×100 mL), sat. $NaHCO_3$ (100 mL), brine (100 mL), dry over $MgSO_4$ and concentrate in vacuo. Slurry the crude solid in cold MeOH (25 mL, 0° C.), filter and air dry to afford (1S-trans)-Methyl 1-(1,3-benzodioxol-5-yl)-2,3-dihydro-3-oxo-5-propoxy-1H-indene-2-carboxylate as a pale yellow solid (4.8 g, 62%): mp 103.0–105.5° C.; $^1$H NMR δ7.15 (d, J=2.3 Hz, 1H), 7.05 (d, J=8.4 Hz, 1H), 6.95 (dd, J=2.4, 8.3 Hz, 1H), 6.7 (m, 2H), 6.45 (d, J=1.2 Hz, 1H), 6.4 (m, 2H), 4.6 (s, 1H 3.9 (t, J=6.5 Hz, 2H), 3.7 (s, 3H), 1.8 (quintet, J=7.2 Hz, 2H), 1.05 (t, J=7.4 Hz, 3H).

(vii). (S)-Methyl 1-(1,3-benzodioxol-5-yl)-3-[(fluorosulfonyl)oxy]-5-propoxy-1H -indene-2-carboxylate (a compound of Formula (h))

A 100 mL three-necked flask under nitrogen was charged with 60% NaH suspension (116 mg, 2.9 mmol), $CH_2Cl_2$ (10 mL) and cooled to 0° C. The mixture was stirred for 0.5 h and warmed to room temperature. A solution of (1S-trans)-methyl 1-(1,3-benzodioxol-5-yl)-2,3 dihydro-3-oxo-5-propoxy-1H-indene-2-carboxylate (710 mg, 1.93 mmol) in $CH_2Cl_2$ (25 mL) was then added dropwise over 15 minutes. After 1 h, the mixture was cooled to 0° C. and fluorosulfonic anhydride (0.3 mL, 2.9 mmol) added in one portion. After 1.5 h the reaction was quenched with 3 M AcOH (1 mL), diluted with EtOH (150 mL) and cooled to 0° C. Filtration of the precipitate afforded (S)-methyl 1-(1,3-benzodioxol-5-yl)-3-[(fluorosulfonyl)oxy]-5-propoxy -1H-indene-2-carboxylate as a pale white solid (494 mg, 55%, 99% e.e.); mp 160.0–161.0° C.; Chiralpak AD column (93:7 IPA/hexane, 1 mL/min, 254 nm, 13.13 min).

(vii)a. (S)-Methyl-1-(1,3-benzodioxol-5-yl)-3-[(fluorosulfonyl)oxy]5-propoxy-1H -indene-2-carboxylate A 500 mL round-bottomed flask was charged with toluene (100 mL) and (1S-trans) -Methyl 1-(1,3-benzodioxol-5-yl)-2,3-dihydro-3-oxo-5-propoxy-1H-indene-2-carboxylate (11.8 g, 0.032 mol). At 10° C., 60% NaH (1.9 g, 0.048 mol) was added portionwise over 0.5 h and the mixture warmed to 40° C. for 1 h. Upon cooling to 0 ° C., disulfuryl fluoride was added (3.45 mL, 0.0032 mol) dropwise over 15 minutes while maintaining the temperature below 10° C. Continue to stir the reaction mixture at room temperature for 1.5 h and cool to 0° C. Add $H_2O$ (150 mL) dropwise to keep the temperature below 5° C. followed by the addition of glacial acetic acid (150 miL). Warm the reaction mixture to room temperature and add THF (3 L) and $H_2O$ (300 mL). Separate the two phases, wash the organic phase with $H_2O$ (2×300 mL) and concentrate to a thick slurry. Add $iPr_2O$ (1 L) and with vigorous stirring cool the slurry to −15° C. After 1 h, filter the slurry and wash the filter cake with cold $iPr_2O$ (−15° C.,1 L). Dry the product to a constant weight to afford (S) -Methyl-1-(1,3-benzodioxol-5-yl)-3-[(fluorosulfonyl)oxy]5-propoxy-1H-indene-2-carboxylate as a pale white solid (9.5 g, 67%): $^1$H NMR δ7.15 (d, J=8.9 Hz, 1H), 7.05 (s, 1H), 6.95 (dd, J=2.3, 8.4 Hz, 1H), 6.7 (m, 2H), 6.45 (s, 1H), 5.9 (m, 2H), 4.85 (s, 1H), 3.95 (t, J=6.5 Hz, 2H), 3.8 (s, 3H), 1.8 (quintet, J=7.8 Hz, 2H), 1.05 (t, J=7.4 Hz, 3H).

(vi) and (vii) can be combined as follows.

A 5 L three-necked flask equipped with air driven stirrer and nitrogen take-off adapter was charged with (S)-3-(1,3-Benzodioxol-5-yl)-2,3-dihydro-6-propoxy-1H -inden-1-one (150 g, 0.483 mol, 90.4% e.e.) and dimethyl carbonate (1.5 L). At 20 ° C., add sodium t-amylate (64 g, 0.580 mol) portionwise (4×16 g) while maintaining the temperature below 35° C. Upon complete addition of base, stir the solution until the temperature drops to 20° C. (~1.5 h). Cool the solution to 0° C. and add a 50% acetic acid solution (300 mL) over 15 minutes to keep the temperature below 5° C. Concentrate the solution to a minimum stir volume, add toluene (1.5 L) and wash with water (2×500 mL). Concentrate the organic phase to a minimum stir volume and perform a toluene azeotrope (3×1 L) to remove residual $H_2O$. Charge additional toluene to a 1.5 L volume and add 60% NaH (29 g, 0.725 mol) at 10° C. over 0.5 h. Warm the mixture to 40° C. for 1 h, then cool the solution to 0° C. and add disulfuryl fluoride (52 mL, 0.483 mol) over 15 minutes while maintaining the temperature below 10° C. Stir the reaction mixture at room temperature for 1.5 h and cool to 0° C. Add $H_2O$ (150 mL) dropwise to keep the temperature below 5° C. followed by the addition of glacial acetic acid (150 mL). Warm to room temperature and add THF (3 L) and $H_2$) (300 mL). Separate the two phases, wash the organic phase with $H_2O$ (2×300 mL) and concentrate to a thick slurry. Add $iPr_2O$ (1 L) and with vigorous stirring cool the slurry to −15° C. After 1 h, filter the slurry and wash the filter cake with cold $iPr_2O$ (−15° C., 1 L). Dry the product to a constant weight to afford (S)-Methyl-1-(1,3-benzodioxol-5-yl)-3-[(fluorosulfonyl)oxy]5-propoxy-1H -indene-2-carboxylate as a pale white solid (126 g, 58%, 94.3% e.e.): mp 161.0-162.0° C. ; Chiralpak AD column (93:7 IPA/hexane, 1 mL/min, 254 nm, 7.05 min: 0.35%, 9.41 min: 12.31%).

(viii). (S)-Methyl 1-(1,3-benzodioxol-5-yl)-3-[4-methoxy-2-(phenylmethoxy)phenyl]-5-propoxy-1H-indene-2-carboxylate (a compound of Formula (i))

A 50 mL three-necked flask under nitrogen was charged with (S)-methyl 1-(1,3-benzodioxol-5-yl)-3-[(fluorosulfonyl)oxy]-5-propoxy-1H-indene-2-carboxylate (600 mg, 1.3 mmol), [4-methoxy-2-(phenylmethoxy)phenyl]boronic acid (Compound (u)) (330 mg, 1.4 mmol), toluene (16 mL), EtOH (2 mL), and Pd(dppf)$Cl_2$ catalyst (4.8 mg, 0.005 mmol). The mixture was stirred for 0.5 h at room temperature followed by the addition of 1.3 M $K_2CO_3$ solution (2.0 mL, 2.6 mmol) and heated to 70° C. for 45 min. The mixture was cooled to room temperature, charged with Norit A charcoal (5 g) and filtered through celite (10 g). The filtrate was then concentrated in vacuo affording (S)-methyl-1-(1,3-benzodioxol-5-yl)-3-[4-methoxy-2-(phenylmethoxy)phenyl]-5-propoxy-1H-indene-2-carboxylate as a yellow gum (731 mg, 99% yield). (viii)a. (S)-Methyl 1-(1,3-benzodioxol-5-yl)-3-[4-methoxy-2-(phenylmethoxy)phenyl]-S-propoxy-1H-indene-2-carboxylate A 500 mL three-necked round-bottomed flask under nitrogen was charged with (S) -Methyl-1-(1,3-benzodioxol-5-y)-3-[(fluorosulfonyl)oxy]5-propoxy-1H-indene-2-carboxylate (10 g, 21.46 mmol), [4-methoxy-2-(phenylmethoxy)phenyl] boronic acid (Compound (u)) (5.53 g, 21.46 mmol), toluene (200 mL), EtOH (16 mL), and Pd(dppf)Cl$_2$ catalyst (78.5 mg, 0.11 mmol). The mixture was stirred for 0.5 h at room temperature followed by the addition of K$_2$CO$_3$ solution (5.92 g in 16 mL H,O, 42.92 mmol) and heated to 70° C. for 45 min. The mixture was cooled to room temperature, washed with H$_2$O (2×50 mL), brine (1×50 mL), dried over MgSO$_4$ and the solvent removed in vacuo. The crude product was purified via recrystallization from 2-methoxy ethanol to afford (S)-Methyl 1-(1,3-benzodioxol-5-yl)-3-[4-methoxy-2-(phenylmethoxy)phenyl]-5-propoxy-1H-indene-2-carboxylate as a light yellow solid (8.7 g, 75% yield): mp 114.0–117.0° C. $^1$H NMR (DMSO, 335 K) δ7.3–7.2 (m, 8H), 7.1 (d, J=8.3 Hz, 1H), 6.9 (dd, J=2.4, 8.2 Hz, 1H), 6.85 (d, J=2.1 Hz, 1H), 6.75 (dd, J=2.3, 8.2 Hz, 1H), 6.65 (d, J=2.3 Hz, 1H), 6.55 ; (d, J=1.5 Hz, 1H), 5.9 (s, 2H), 5.1 (s, 2H), 4.9 (s, 1H), 3.9–3.8 (m, 5H), 3.4 (s, 3H), 1.65 (quintet, J=7.8 Hz, 2H), 0.9 (t, J=7.4 Hz, 3H)

(ix). Methyl (1S, 2S, 35)-1-(3, 4-methylenedioxyphenyl)-3-(4-methoxy-2-phenol) -5-propoxyindane-2-carboxylate (a compound of Formula (j))

A 125 mL Paar hydrogenation bottle was charged with (S)-methyl 1-(1,3-benzodioxol-5-yl)-3-[4-methoxy-2-(phenylmethoxy)phenyl]-5-propoxy-1H-indene-2-carboxylate (720 mg, 1.3 mmol), EtOAc (10 mL), EtOH (5 mL), conc. HCl (0.73 mL, 0.65 mmol) and 20% Pd(OH)$_2$ on carbon (216 mg, 30% wt, Aldrich). The vessel was placed under hydrogen (70 psi) for 5 h at room temperature. The reaction mixture was then filtered through celite (10 g), and the filtrate partitioned with deionized H$_2$O (20 mL) and EtOAc (20 mL). The organic phase was washed with brine (30 mL), dried (MgSO$_4$) and concentrated in vacuo to afford methyl (1S, 2S, 3S)-1-(3, 4-methylenedioxyphenyl)-3-(4-methoxy-2-phenol)-5-propoxyindane-2-carboxylate as a pale yellow solid (600 mg, 95%).

(ix)a. Methyl (1S,2S,3S)-1-(3,4-methylenedioxyphenyl)-3-(4-methoxy-2-phenol) -5-propoxyindane-2-carboxylate A 250 mL Paar hydrogenation bottle was charged with (S)-Methyl 1-(1,3-benzodioxol-5-yl)-3-[4-methoxy-2-(phenylmethoxy)phenyl]-5-propoxy-1H-indene -2-carboxylate (12.6 g, 22.75 mmol), 2-methoxy ethanol (100 mL), EtOH (100 mL), AcOH (glacial) (10 mL) and 10% Pd(OH)$_2$ on carbon (3.2 g, 25% wt, Aldrich). The vessel was placed under hydrogen (80 psi) for 5 h at room temperature. The reaction mixture was then filtered through celite (20 g), and the filtrate washed with H$_2$O (2×30 ML), brine (30 mL), dried over MgSO$_4$ and concentrated in vacuo. The crude product was dissolved in MeOH (50 mL) and seeded with Methyl (1S,2S,3S)-1-(3,4-methylenedioxyphenyl)-3-(4-methoxy-2-phenol)-5-propoxyindane-2-carboxylate (0.1 g) to form a thick white precipitate. The slurry was cooled to −5° C. for 8 h, filtered and washed with cold MeOH (3×6 mL, 0° C.) to afford Methyl (1S,2S,3S) -1-(3,4-methylenedioxyphenyl)-3-(4-methoxy-2-phenol)-5-propoxy-indane-2-carboxylate as a white solid (7.14 g, 67%, 99.9% e.e.): $^1$H NMR δ7.25 (d, J=8.5 Hz, 1H), 7.05 (d, J=9.0 Hz, 1H), 6.85–6.7 (m, 5H), 6.65 (br s, 1H), 6.45 (dd, J=2.5, 8.5 Hz, 1H), 6.35 (d, J=2.5 Hz, 1H), 5.95 (s, 2H), 4.95 (d, J=7.2 Hz, 1H), 4.7 (d, J=7.5 Hz, 1H), 4.0 (t, J=7.5 Hz, 1H), 3.9 (t, J=6.7 Hz, 2H), 3.75 (s, 3H), 3.1 (s, 3H), 1.9 (quintet, J=6.9 Hz, 2H), 1.1 (t, J=7.4 Hz, 3H).

From procedure (viii), (S)-Methyl 1-(1,3-benzodioxol-5-yl)-3-[4methoxy-2-(phenyl methoxy)phenyl]-5-propoxy-1H-indene-2-carboxylate can be used without purification in procedure (ix) to afford Methyl (1S,2S,3S)-1-(3,4-methylenedioxyphenyl)-3-(4-methoxy-2-phenol)-5-propoxyindane-2-carboxylate in good yield as follows:

A 1 L three-necked round-bottomed flask under nitrogen was charged with (S) -Methyl-1-(1,3-benzodioxol-5-yl)-3-[(fluorosulfonyl)oxy]-5-propoxy-1H-indene-2-carboxylate (30 g, 0.064 mol), [4methoxy-2-(phenylmethoxy)phenyl] boronic acid (Compound (u)) (16.6 g, 0.064 mol), toluene (450 mL), EtOH (50 mL), and Pd(dppf)Cl$_2$ catalyst (0.235 g, 0.32 mmol). The mixture was stirred for 0.5 h at room temperature followed by the addition of K$_2$CO$_3$ solution (17.75 g in 50 mL H$_2$O, 0.129 mol) and heated to 70° C. for 45 min. The mixture was cooled to room temperature, washed with H$_2$O (2×100 mL), brine (1×100 mL) and the solvent removed under reduced pressure to ⅙ volume (50 mL). Transfer the concentrate to a 500 mL Paar hydrogenation bottle and charge with EtOAc (80 mL), EtOH (80 mL), conc. HCl (0.25 mL) and 20% Pd(OH)$_2$ on carbon (15 g, 42% wt, Aldrich). The vessel was placed under hydrogen (80 psi) for 24 h at room temperature. The reaction mixture was then filtered through celite (60 g), and the filtrate washed with H$_2$O (50 mL), brine (50 mL), dried over MgSO, and concentrated in vacuo. The crude product was dissolved in MeOH (100 mL) and seeded with Methyl (1S,2S,3S)-1-(3,4-methylenedioxyphenyl)-3-(4-methoxy-2-phenol)-5-propoxyindane-2-carboxylate (0.1 g) to form a thick white precipitate after vigorous stirring for 3 h at room temperature. The slurry was cooled to −5° C. for 30 h, filtered and washed with cold MeOH (2×10 mL, 0° C.) to afford Methyl (1S,2S,3S)-1-(3,4-methylenedioxyphenyl)-3-(4-methoxy-2-phenol)-5-propoxy-indane-2-carboxylate as a white solid (21.95 g, 72%, 99.9% e.e.); mp 92.0–94.0° C.

(x). (+) (1S, 2R, 3S)-3-(2-Carboxymethoxy-4-methoxyphenyl)-1-(3,4 -methylenedioxyphenyl)-5-(prop-1-yloxy)indane-2-carboxylic acid (a compound of Formula (6))

Methyl (1S, 2S, 3S)-1-(3, 4-methylenedioxyphenyl)-3-(4-methoxy-2-phenol)-5-propoxyindane-2-carboxylate (0.1 g) in dry THF (2mL) is added to potassium carbonate (6 mg) in a small volume of dry THF at 0° C. The mixture was stirred at 0° C. for 15 min. and ethyl bromoacetate is then added (42 mg). The resulting mixture was stirred at 0° C. for 1 h. In a separate container 1 mL of DI water is combined with lithium hydroxide monohydrate (3 mg). The mixture was stirred to dissolve all the solids. When a homogeneous solution is obtained, the lithium hydroxide solution is added to the reaction mixture. The mixture is heated to 50° C. and stirred for 2 h. The reaction is allowed to cool to room temperature. DI water (2 mL) is added followed by toluene (20 mL) and citric acid (4 mg) and the resulting mixture stirred for 5 minutes. The organic layer is washed with brine and evaporated to yield title compound.

(xi). (+) (1S, 2R, 3S)-3-(2-Carboxymethoxy-4-methoxyphenyl)-1-(3,4-methylenedioxyphenyl)-5-(prop- 1-yloxy)indane-2-carboxylic acid disodium salt (a compound of Formula (7)).

A solution of (+) (1S, 2R, 3S)-3-(2-carboxymethoxy-4-methoxyphenyl)-1-(3,4-methylenedioxyphenyl)-5-(prop-1-yloxy)indane-2-carboxylic acid in absolute ethanol/water (12 to 1) was titrated to pH=11–12 with 1.25 N sodium hydroxide solution then after stirring for 15 minutes, concentrated to an oil. Absolute ethanol was added and the solution reconcentrated to a solid which was triturated with hexane, and filtered. The solid was dried to constant weight to afford (+) (1S, 2R, 3S)-3-(2-Carboxymethoxy-4-methoxyphenyl)-1-(3,4-methylenedioxyphenyl)-5-(prop-1-yloxy)indane-2-carboxylic acid disodium salt.

Example 2

Corresponding to Scheme 2

(+) (1S, 2R, 3S)-3-[2-(2-Hydroxyeth-1-yloxy)-4-methoxyphenyl]-1-(3,4-methylenedioxyphenyl)-5-(prop-1-yloxy)indane-2-carboxylic acid ethylene diamine salt (2:1)

(i). (S)-Methyl 1-(1,3-benzodioxol-5-yl)-3-[4-methoxy-2-[2-(phenylmethoxy)ethoxy]phenyl]-5-propoxy-1H-indene-2-carboxylate (a compound of Formula (m))

A 50 mL three-necked flask under nitrogen was charged with (S)-methyl 1-(1,3-benzodioxol-5-yl)-3-[(fluorosulfonyl)oxy]-5-propoxy-1H-indene-2-carboxylate (prepared as described in Example 1 (vii)) (500 mg, 1.07 mmol), (4-methoxy-2-[2-(phenylmethoxy)ethoxy]phenyl] boronic acid (Compound (v)) (330 mg, 1.09 mmol), toluene (15 mL), EtOH (1 mL), and Pd(dppf)Cl$_2$ catalyst (24 mg, 0.033 mmol). The mixture was stirred for 0.5 h at room temperature followed by the addition of 1.3 M K$_2$CO$_3$ solution (1.0 mL, 1.3 mmol) and heated to 70° C. for 45 min. The mixture was cooled to room temperature, charged with Norit A charcoal (5 g) and filtered through celite. The filtrate was then concentrated in vacuo affording (S)-methyl 1-(1, 3-benzodioxol-5-yl)-3-[4-methoxy-2-[2-(phenylmethoxy) ethoxy]phenyl]-5-propoxy-1H-indene-2-carboxylate as a yellow gum (640 mg, 98% yield).

(ii). [1S-(1α, 2α,3α)]-Methyl 1-(1,3-benzodioxol-5-yl)-2,3-dihydro-3-[2-(2-hydroxyethoxy-)-4-methoxyphenyl]-5-propoxy-1H-indene-2-carboxylate (a compound of Formula (n))

A 125 mL Paar hydrogenation bottle was charged with (S)-methyl 1-(1,3-benzodioxol-5-yl)-3-[4-methoxy-2-[2-(phenylmethoxy)ethoxy]phenyl]-5-propoxy -1H-indene-2-carboxylate (630 mg, 1.3 mmol), EtOAc (10 mL), EtOH (5 mL), conc. HCl (0.73 mL, 0.65 mmol) and 20% Pd(OH)$_2$ on carbon (189 mg, 30% wt, Aldrich). The vessel was placed under hydrogen (70 psi) for 5 h at room temperature. The reaction mixture was then filtered through celite (10 g), and the filtrate partitoned with deionized H$_2$O (20 mL) and EtOAc (20 mL). The organic phase was washed with brine (30 mL), dried (MgSO$_4$) and concentrated in vacuo to afford [1S -(1α, 2α, 3α)]-methyl 1-(1,3-benzodioxol-5-yl)-2,3-dihydro-3-[2-(2-hydroxyethoxy) -4-methoxyphenyl]-5-propoxy-1H-indene-2-carboxylate as a pale yellow solid (650 mg, 95%).

(iii). (+) (1S, 2R, 3S)-3-[2-(2-Hydroxyeth-1-yloxy)-4-methoxyphenyl]-1-(3,4 -methylenedioxyphenyl)-5-(prop-1-yloxy)indane-2-carboxylic acid (a compound of Formula (8))

A 10 mL three-necked flask equipped with reflux condenser was charged with [1S -(1α, 2α, 3α)]-methyl 1-(1,3-benzodioxol-5-yl)-2,3-dihydro-3-[2-(2-hydroxyethoxy)-4-methoxyphenyl]-5-propoxy-1H-indene-2-carboxylate (34 mg, 0.071 mmol), THF (1 mL), MeOH (0.5 mL) and LiOH—H$_2$O (15 mg, 0.355 mmol). The solution was heated to reflux for 12 h, cooled to room temperature and acidified with citric acid monohydrate (40 mg, 0.19 mmol) to pH 3.0. Upon complete hydrolysis, EtOAc (20 mL) and H$_2$O (20 mL) was added, the organic phase washed with brine (15 mL), dried (MgSO$_4$) and concentrated in vacuo affording (+) (1S, 2R, 3S)-3-[2-(2-hydroxyeth-1-yloxy)-4methoxyphenyl]-1-(3,4-methylenedioxyphenyl)-5-(prop-1-yloxy)indane-2-carboxylic acid as a white solid (30 mg, 81%).

(iv). (+) (1S, 2R, 3S)-3-[2-(2-Hydroxyeth-1-yloxy)-4-methoxyphenyl]-1-(3,4 - methylenedioxyphenyl)-5-(prop-1-yloxy)indane-2-carboxylic acid ethylene diamine salt (2: 1) (a compound of Formula (9)

A 10 gallon glass-lined reactor (R-104) was charged with a toluene solution of (+)(1S,2R,3S)]-3-[2-(2-hydroxyeth-1-yloxy)-4-methoxyphenyl]-1-(3,4 -methylenedioxyphenyl)-5-(prop-1-yloxy)indane-2-carboxylic acid via a 1 micron in-line filter. The line and filter were rinsed with toluene and the rinse added to the reactor: The organic solution was concentrated under reduced pressure. Distillation was discontinued and 2-propanol added to the concentrate. The organic solution was concentrated again under reduced pressure. Distillation was discontinued and 2-propanol added to the concentrate. The resulting solution in 2-propanol was allowed to stir at ambient temperature for approximately 15 minutes to obtain a homogeneous mixture. Via a 1 micron in-line filter, the contents of R-104 were transferred via vacuum into a glass lined reactor (R-102). The reactor R-104, filter and lines were washed with 2-propanol and the wash added to the contents of R-102. Additional 2-propanol was charged to R-102 (via a 1 micron in-line filter). The contents of R-102 were heated to approximately 61° C. over a period of 15–20 minutes under a gentle purge of nitrogen. Heating was discontinued and ethylene diamine was added. The reaction mixture was cooled to 30–35° C. over a period of 3 hours. As the solution cooled to 57° C., precipitation of the title compound occurred. The resulting slurry was stirred at 30–35° C. for approximately 60 minutes before isolation of the title compound via centrifugation. The product was washed with 3 portions of 2-propanol followed by hexanes chilled to 0–5° C. The product was dried in the vacuum oven for approximately 48 hours at 20–25° C. to afford the title compound.

Example 3

(+) (1S, 2R, 3S)-3-[2-(2-Hydroxyeth-1-yloxy)-4-methoxyphenyl]-1-(3,4-methylenedioxyphenyl) -5-(prop-1-yloxy)indane-2-carboxylic acid ethylene diamine salt (2: 1)

(i) A 500 mL flask was charged with 150 mL of toluene followed by ethylene carbonate (29.4 g, 98%, 327 mmol) and 15.9 g (97.4%, 32.6 mmol) of methyl -(1S,2S,3S)-1-(3,4-methylenedioxyphenyl)-3-(4-methoxy-2-hydroxyphenyl)-5-propoxyindane-2-carboxylate (a compound of Formula (i) prepared as in step (vii) of Example 1). With moderate agitation at ambient temperature, potassium carbonate (23.1 g, 98%, 163.8 mmol) was added. Under an atmosphere of nitrogen and with moderate agitation, the contents of the flask were heated to approximately 112° C. After approximately 3 hours at or around 112° C., the reaction was cooled to 25–30° C. over a period of 20 minutes, and DI water (120 mL) was added. The mixture was stirred then the aqueous layer was separated. The organic phase was concentrated to a gum under reduced pressure then diluted with methanol (50 mL) and tetrahydrofuran (80 mL). A solution of lithium hydroxide monohydrate, 4.5 g (477.8 mmol) dissolved in 50 mL of water was then added. The reaction mixture was heated to reflux (internal temperature 62–65° C.) over approximately 15 minutes and maintained at reflux while monitoring the reaction progress by HPLC. The reaction was considered complete when no intermediates were detected by HPLC analysis. After approximately 60 minutes at reflux the reaction was considered complete and the contents of the flask cooled to ambient and the reaction mixture concentrated under reduced pressure. Toluene (150 mL), water (150 mL) followed by citric acid (15 g) was then added to the resulting solution and the mixture stirred for approximately 15 minutes. The bottom aqueous layer was drained and the organic layer was washed with aqueous brine solution (100 mL). The organic layer was drained from the flask, then concentrated in vacuo to afford 16.2 g of the free acid of the title compound as a foam.

HPLC wt/wt assay indicated 90.5% purity for a corrected yield of 88.8%. An analytical sample could be obtained by recrystallization from 2-propanol. Mpt. 125–127° C.

(ii) A toluene solution of (+)(1S,2R,3S)]-3-[2-(2-hydroxyeth-1-yloxy)-4-methoxyphenyl]-1-(3,4-methylenedioxyphenyl)-5-(prop-1-yloxy)indane-2-carboxylic acid (868.8 g @ 11.2% wt/wt, 192.5 mmol) was concentrated under reduced pressure to a volume of approximately 200 mL. Distillation was discontinued and 2-propanol (500 mL) added to the concentrate. The organic solution was concentrated again under reduced pressure to a volume of approximately 200 mL. Distillation was discontinued and 2-propanol (500 mL) added to the concentrate. The resulting solution in 2-propanol was allowed to stir at ambient temperature for approximately 15 minutes to obtain a homogeneous mixture then diluted with an additional 1000 mL of 2-propanol. The resulting solution was heated to approximately 60° C. over a period of 15–20 minutes under a gentle purge of nitrogen. Heating was discontinued and ethylene diamine (11.6 g, 99.5 +%. 192.5 mmol) was added. The reaction mixture was cooled to 30–35° C. over a period of 4 hours. As the solution cooled to 57° C., precipitation of the title compound occurred. The resulting slurry was stirred at ambient temperature for approximately 12 hours then cooled to 0° C. an additional 3 hours before isolation of the title compound via filtration. The product was washed with 3 portions of 2-propanol (300 mL) followed by hexane's (600 mL) chilled to 0–5° C. The product was dried in the vacuum oven for approximately 16 hours at 20–25° C. to afford 91.6 (87%) of the title compound.

Anal Calcd. for C30H34NO8 C, 67.15;H, 6.39; N, 2.61. Found, C, 67.2; H,6.48; N, 2.67.

Example 4

4-Methoxy-2(phenylmethoxy)phenyl]boronic acid (a compound of Formula (u))

(i) 1-Bromo-4-methoxy-2-(phenylmethoxy)benzene (a compound of Formula (aa))

A 12 L four-necked round-bottomed flask equipped with mechanical stirrer, thermometer and reflux condenser with nitrogen inlet was charged with 2-bromo-5-methoxyphenol (615 g, 2.98 mol), $CH_3CN$ (6 L), $K_2CO_3$ (671 g, 4.77 mol), benzyl chloride (363 mL, 3.14 mol), and KI (6 g, 0.036 mol). The mixture was heated to reflux for 3 h, cooled to room temperature, and $H_2O$ (3 L) added to form a biphasic mixture. The aqueous layer was separated, $CH_3CN$ (3 L) removed in vacuo and EtOAc (4 L) added to extract the product. After a wash with $H_2O$ (3 L) and 10% NaCl solution (1.8 L), the organic layer was concentrated to dryness to afford 1-bromo-4-methoxy-2-(phenylmethoxy)benzene as a light yellow oil (895.5 g, 99%): 110° C. (2.5 mm Hg); $^1$H NMR δ7.55–7.25 (m, 6H), 6.55 (d, J=2.7 Hz, 1H), 6.35 (dd, J=8.5 Hz, 1.5 Hz, 1H), 5.1 (s, 2H), 3.75 (s, 3H).

(ii) [4-methoxy-2(phenylmethoxy)phenyl]boronic acid (a compound of Formula (u))

A 2 L three-necked flask equipped with thermometer, reflux condenser and mechanical stirrer was charged with 1-bromo4-methoxy-2-(phenylmethoxy)benzene (43.0 g, 0.147 mol), anhydrous THF (600 mL) under nitrogen. Magnesium turnings (4.2 g, 0.17 mol) and 1,2-dibromoethane (0.5 mL, 6 mmol) was then added and the mixture heated to reflux. After 1.5 h, the reaction was cooled to −78° C. and $B(OMe)_3$ (33.4 mL, 0.294 mol) added dropwise while maintaining an internal temperature below −60° C. Upon complete addition, the reaction was quenched with 5% HCl (15 mL) to pH=3.0, partioned with EtOAc (100 mL), the organic phase separated, washed with brine (100 mL), dried ($MgSO_4$) and concentrated in vacuo giving a pale yellow solid. The solid was triturated with hexane (90 mL), filtered and dried to afford [4-methoxy-2(phenylmethoxy)phenyl]boronic acid as a pale white solid (32 g, 85%): mp 127.0–129.0° C.; $^1$H NMR δ7.8 (d, 3=8.2 Hz, 1H), 7.5–7.3 (m, 5H), 6.6 (dd, J=8.2, 2.7 Hz, 1H), 6.55 (d, J=5 Hz, 1H), 5.65 (s, 2H), 5.15 (s, 2H), 3.85 (s, 3H).

Example 5

[4-Methoxy-2-[2-(phenylmethoxy)ethoxy]phenyl] boronic acid (a compound of Formula (v))

(i) 1-Bromo-4-methoxy-2-[2-(phenylmethoxy ethoxy] benzene (a compound of Formula (ab))

A 1 L three necked flask equipped with addition funnel was charged with 2-bromo -5-methoxyphenol (82.5 g, 0.4 mol) in DMF (600 mL) and treated with solid $K_2CO_3$ (61.75 g, 0.44 mol). The mixture was heated to 65° C. and benzyloxyethyl bromide (91.7 g, 0.42 mol) added dropwise over 30 minute period. After 2h the mixture was cooled to room temperature, filtered, and the filtrate partitioned with EtOAc (1 L) and $H_2O$ (1 L). The combined organic phases were washed with $H_2O$ (250 mL), brine (250 mL), dried ($MgSO_4$) and concentrated in vacuo to afford the crude product as a tan oil (142 g). The oil was vacuum distilled (135° C./5 mm Hg) to afford 1-bromo-4-methoxy-2-[2-(phenylmethoxy) ethoxy]benzene as a colorless oil (125 g, 83%): $^1$H NMR δ7.45–7.25 (m, 6H), 6.55 (d, J=2.7 Hz, 1H), 6.4 (dd, J=8.6, 2.7 Hz, 1H), 4.7 (s, 2H), 4.2 (t, J=5.0 Hz, 2H), 3.9 (t, J=5.0 Hz, 2H), 3.75 (s, 3H).

(ii) [4-Methoxy-2-[2-(phenylmethoxy)ethoxy]phenyl] boronic acid (a compound of Formula (v))

A 500 mL three-necked flask equipped with thermometer, reflux condenser and mechanical stirrer was charged with 1-bromo-4methoxy-2-[2-(phenylmethoxy ethoxy]benzene (14.8 g, 0.042 mol), anhydrous THF (90 mL) under nitrogen. Magnesium turnings (1.1 g, 0.046 mol) and 1,2-dibromoethane (0.1 mL, 1.2 mmol) was then added and the mixture heated to reflux. After 1.5 h, the reaction was cooled to −78° C. and B(OMe)$_3$ (7.15 mL, 0.063 mol) added dropwise while maintaining an internal temperature below −60° C. Upon complete addition, the reaction was quenched with 5% HCl (5 mL) to pH=3.0, partioned with EtOAc (50 mL), the organic phase separated, washed with brine (50 mL), dried (MgSO$_4$) and concentrated in vacuo giving a pale yellow solid. The solid was triturated with hexane (30 mL), filtered and dried to afford [4-methoxy-2-[2-(phenylmethoxy) ethoxy]phenyl]boronic acid as a pale white solid (10.9 g 82%): mp 99.0–101.0° C.; $^1$H NMR δ7.8 (d, J=8.2 Hz, 1H), 7.4–7.2 (m, 5H), 6.6 (d, J=8.2 Hz, 1H), 6.45 (s, 1H), 5.8 (s, 2H), 4.6 (s, 2H), 4.2 (m, 2H), 3.8 (s, 3H).

Example 6

(+) (1S, 2R, 3S)-3-(2-Carboxymethoxy-4methoxyphenyl)-1-(3,4-methylenedioxyphenyl)-5-(prop-1-yloxy)indane-2-carboxylic acid disodium salt (i) (+) (1S, 2R, 3S)-3-(2-Carboxymethoxy-4-methoxyphenyl)-1-(3,4-methylenedioxyphenyl)-5-(prop-1-yloxy)indane-2-carboxylic acid disodium salt (a compound of Formula (7)).

A 5 L 3 necked round-bottom flask equipped with an air driven stirrer, and a nitrogen inlet/outlet was charged with 212.0 g (98.4% wt/wt, 437.8 mmol) of the compound of Example 1, step (ix), 2120 mL of acetone and 212 mL of methanol. The resulting slurry/solution was degassed for approximately 10 minutes under house vacuum. After releasing the vacuum and flushing the flask with nitrogen, 302.5 g (2.19 moles) of potassium carbonate followed by 87.1 g (546.6 mmol) of methyl bromoacetate were added in single portions. The resulting slurry was stirred at ambient temperature under an atmosphere of nitrogen while the progress of the reaction was monitored by HPLC. The reaction was deemed to be complete when all the starting material had been converted to the title compound. The slurry was filtered through 300 g of Aluminium oxide rinsing with 1250 mL of acetone. The resulting filtrate was concentrated under reduced pressure to a volume of approximately 500 mL. The concentrate was diluted with 2000 mL of t-butyl methyl ether (TBME) then washed with 2×1000 mL portions of 5% aqueous citric acid followed by 1000 mL of saturated aqueous brine to afford 1720 g of (+) -methyl-(1S,2S,3S)-5-propoxy-1-(3,4-methylenedioxy-phenyl)-3-(2-carbomethoxy]methoxy-4methoxyphenyl)indane-2-carboxylate (the cis alkylated diester intermediate to the title compound) as a solution in TBME. Analysis indicated 15.6% wt/wt and 98.5% PAR by HPLC. An analytical sample could be obtained by crystallization of a concentrate from a mixture of hexane's and TBME. $^1$H NMR (CDCl$_3$), δ7.36 (d, 1H), 7.07 (d, 1H), 6.73–6.88 (m, 5H), 6.49 (q, 1H), 6.37 (d, 1H), 5.94 (s, 2H), 5.17 (d, 1H), 4.68–4.74 (m, 3H), 4.02 (t, 1H), 3.90 (t 2H), 3.81 (s, 3H), 3.75 (s, 3H), 2.97 (s, 3H), 1.75–1.87 (m, 2H), 1.0 (t, 3H)ppm.

Saponification/epimerization of (+)-methyl-(1S,2S,3S)-5-Propoxy-1-(3,4-methylenedioxy-phenyl)-3-(2-carbomethoxy]methoxy-4-methoxyphenyl)indane-2-carboxylate to (+)-(1S,2R,3S)-5-Propoxy-1-(3,4-methylenedioxy-phenyl)-3-(2-carbomethoxy]methoxy-4-methoxyphenyl)indane-2-carboxylic acid was effected by concentration of the TBME solution, dilution with 2-propanol and water and subsequent treatment with an excess of 50% aqueous sodium hydroxide solution (25 equivalents). When the saponification/epimerization was deemed complete, the mixture was acidified with 6N aqueous HCl. Subsequent extractive work-up afforded the diacid intermediate of title compound as a solution in TBME. Treatment of the diacid with sodium hydroxide afforded the above depicted compound predominately as the single enantiomer.

While the preferred embodiments of the invention are illustrated by the above, it is understood that the invention is not limited to the precise instructions herein disclosed and that the right to all modifications coming within the scope of the following claims is reserved.

What is claimed is:

1. A compound of the Formula (u):

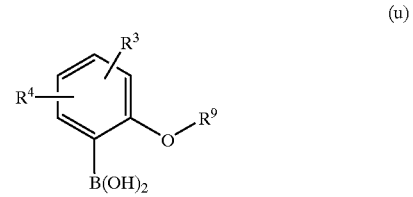

where $R^3$ and $R^4$ are independently H, OH, protected OH, $C_{1-8}$alkoxy, I, Br, Cl, F, $CF_3$ or $C_{1-6}$alkyl and $R^9$ is an oxy protecting group.

2. A compound of Formula (v):

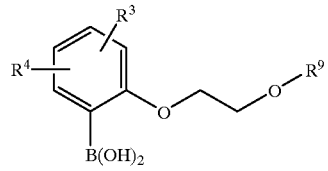

where $R^3$ and $R^4$ are independently H, OH, protected OH, $C_{1-8}$alkoxy, I, Br, Cl, F,$CF_3$ or $C_{1-6}$alkyl and $R^9$ is an oxy protecting group.

3. A process for the preparation of a compound of the Formula,

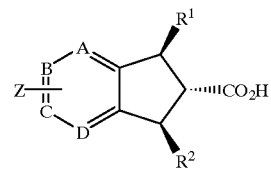

where three of A, B, C and D are carbon atoms and one is a nitrogen atom;

$R^1$ is

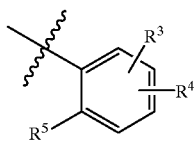

where $R^3$ and $R^4$ are independently H, OH, protected OH, $C_{1-8}$alkoxy, I, Br, Cl, F, $CF_3$ or $C_{1-6}$alkyl and $R^5$ is —$OCH_2CO_2H$;

$R^2$ is

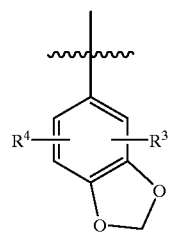

where $R^3$ and $R^4$ are as indicated above and

Z is H, OH, or $C_{1-5}$alkoxy;

or a pharmaceutically acceptable salt thereof, which comprises converting a compound of formula (u), as described in claim 1, into a compound of the above Formula and thereafter optionally forming a pharmaceutically acceptable salt thereof.

4. A process for the preparation of a compound of the Formula,

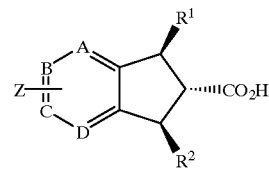

where three of A, B, C and D are carbon atoms and one is a nitrogen atom;

$R^1$ is

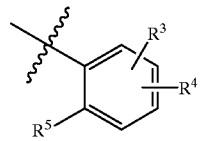

where $R^3$ and $R^4$ are independently H, OH, protected OH, $C_{1-8}$alkoxy, I, Br, Cl, F, $CF_3$ or $C_{1-6}$alkyl and $R^5$ is —$OCH_2CO_2H$;

$R^2$ is

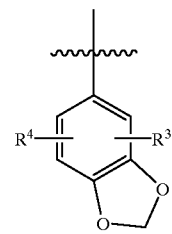

where $R^3$ and $R^4$ are as indicated above and

Z is H, OH, or $C_{1-5}$alkoxy;

or a pharmaceutically acceptable salt thereof, which comprises converting a compound of formula (v), as described in claim 2, into a compound of the above Formula, and thereafter optionally forming a pharmaceutically acceptable salt thereof.

* * * * *